United States Patent [19]

Hoenig

[11] Patent Number: 5,195,982
[45] Date of Patent: Mar. 23, 1993

[54] HYPODERMIC NEEDLE AND PROTECTIVE CAP HANDLING METHOD

[76] Inventor: John R. Hoenig, 7224 McLaren Ave., West Hills, Calif. 91307

[21] Appl. No.: 730,578

[22] Filed: Jul. 15, 1991

Related U.S. Application Data

[63] Continuation of Ser. No. 406,167, Sep. 12, 1989, abandoned.

[51] Int. Cl.$^5$ .............................................. A61M 5/32
[52] U.S. Cl. .................................... 604/192; 604/198; 604/263
[58] Field of Search ................ 604/192, 197, 198, 263

[56] References Cited

U.S. PATENT DOCUMENTS

| | | | |
|---|---|---|---|
| 4,485,918 | 12/1984 | Mayer | 206/366 |
| 4,596,562 | 6/1986 | Vernon | 604/192 |
| 4,654,034 | 3/1987 | Masters | 604/192 |
| 4,659,330 | 4/1987 | Nelson et al. | 604/192 |
| 4,664,259 | 5/1987 | Landis | 206/365 |
| 4,717,386 | 1/1988 | Simmons | 604/192 |
| 4,915,698 | 4/1990 | Levenson | 604/192 |
| 4,938,514 | 7/1990 | D'Addezio | 604/192 |
| 4,955,866 | 9/1990 | Corey | 604/192 |
| 5,037,400 | 8/1991 | Curry | 604/192 |

FOREIGN PATENT DOCUMENTS 8912474 12/1989 World Int. Prop. O. .......... 604/192

Primary Examiner—Stephen C. Pellegrino
Assistant Examiner—Michael Rafa

[57] ABSTRACT

A method for safely uncapping and recapping a hypodermic needle utilizing a needle cap holding device (82) which attaches to an existing hypodermic needle cap (73) by cap gripping end (74). Handle (76) extends a sufficient distance away from said needle cap to allow one hand to support and hold the attached needle cap by the handle. The other hand is free to hold the hypodermic syringe (71) and withdraw it from said needle cap or reinsert into said needle cap keeping the hands a safe distance the hypodermic needle (72) at all times. After the needle cap is reinstalled said handle can be retracted and attached to said syringe by plunger clamping device (88) for positive retention of said needle cap and for storage. In an alternate embodiment, cap holding tool (32) is utilized which has a handle (33) and a controllable gripping means (41) which allows the user to selectively grip and release said needle cap. The user holds said handle and releases said gripping means with one hand. With the other hand the user inserts the needle cap/syringe combination into the aperture (39) of the holding tool and contracts said gripping means with the tool holding hand causing a positive retention of said needle cap in said tool. The user then withdraws said syringe and the attached needle from the retained needle cap with the syringe holding hand. To recap the syringe, the user holds the handle of the holding tool with one hand said cap still being retained. He then inserts said needle into the opening of said cap by holding said syringe with the other hand using a joining motion. When said cap installed back on said syringe, the user releases said gripping means and withdraws the entire syringe and re-attached needle cap. The recoiling device (43) allows said tool to be stored on the users body ready for immediate use. In an alternate embodiment, pocket needle cap tool (48) can be carried in the pocket available for immediate use.

10 Claims, 20 Drawing Sheets

FIGURE 11
FIGURE 12
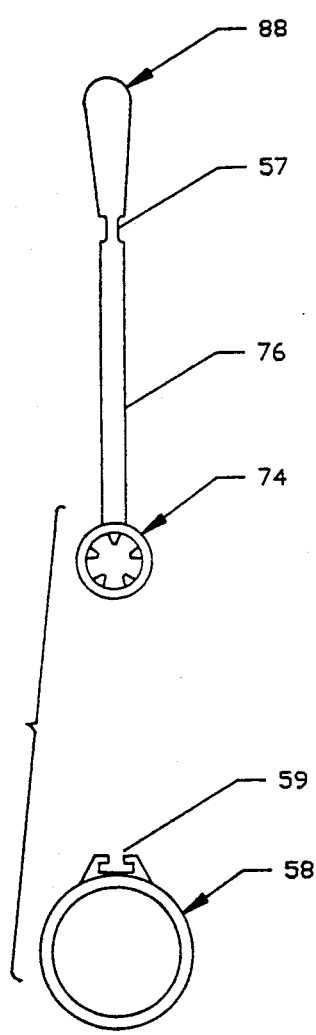
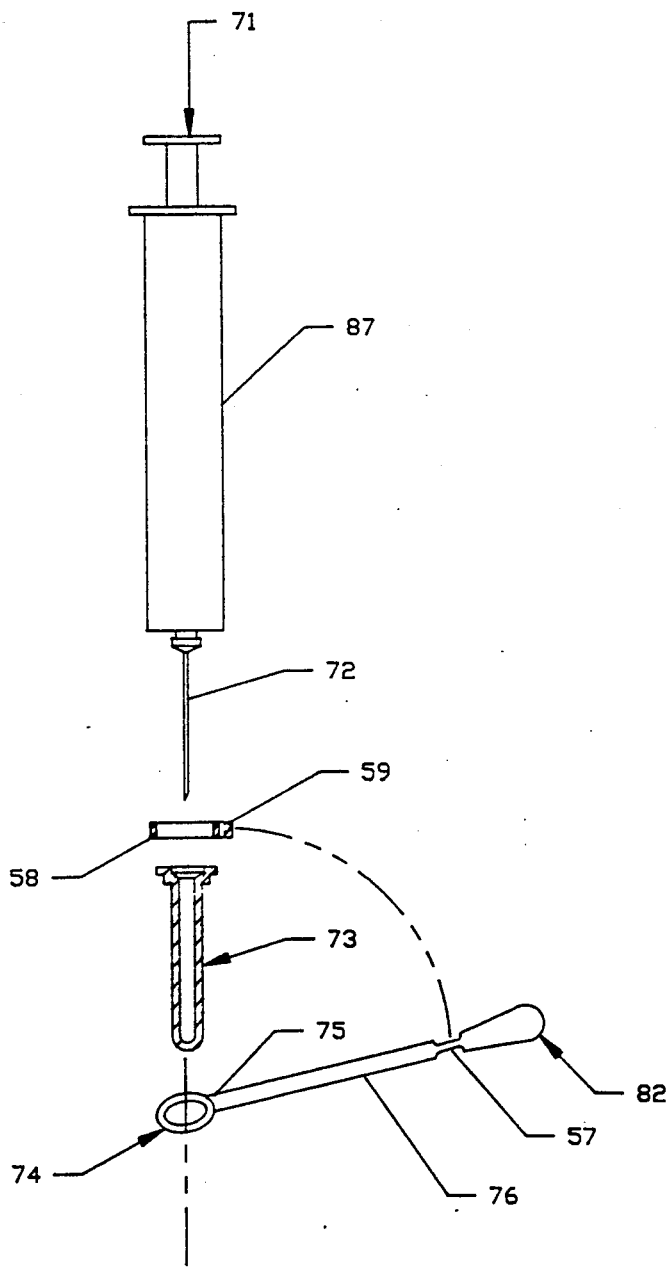

FIGURE 13
FIGURE 14
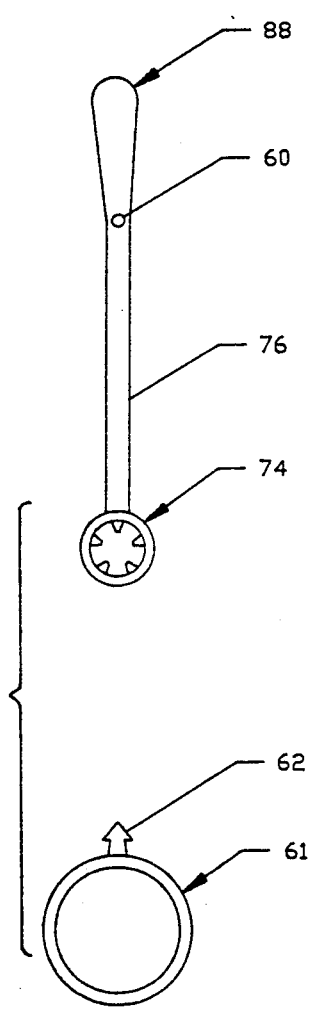
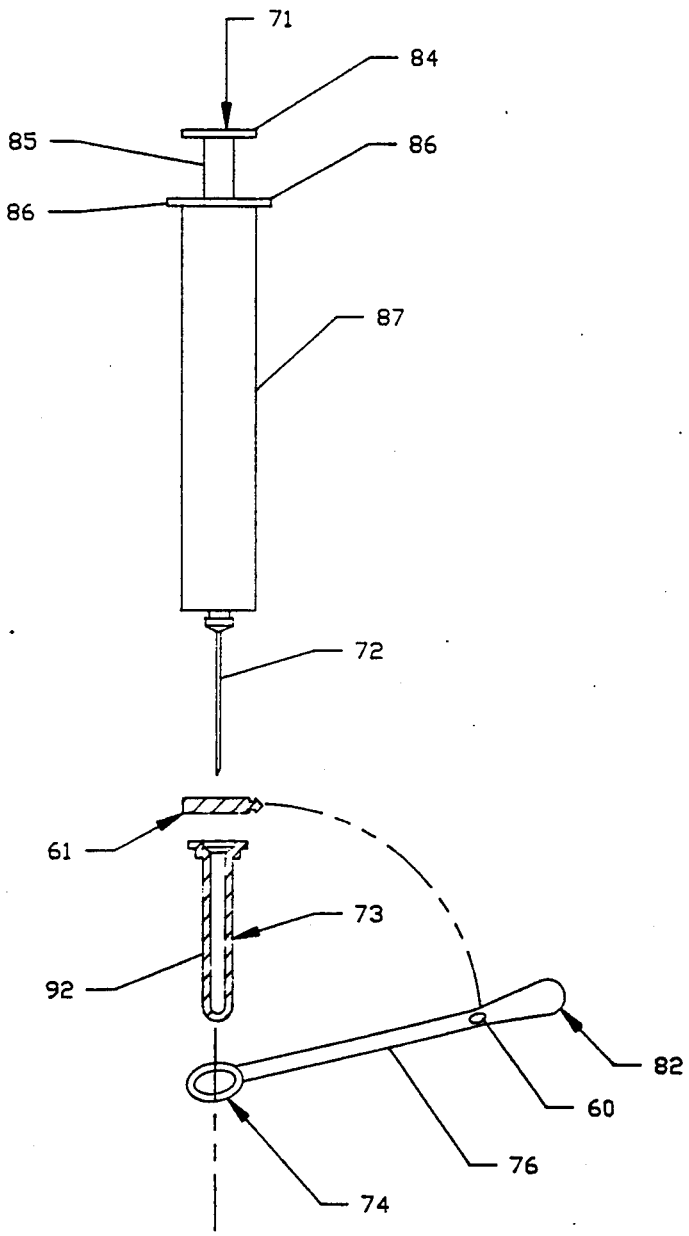

HYPODERMIC NEEDLE AND PROTECTIVE CAP HANDLING METHOD

This application is a continuation of Ser. No. 07/406,167 filed Sep. 12, 1989, abandoned.

BACKGROUND—FIELD OF INVENTION

This invention relates to safe methods and devices for uncapping and recapping hypodermic syringe needles and the prevention of accidental contaminated needle punctures.

BACKGROUND—DESCRIPTION OF PRIOR ART

Hypodermic syringe manufacturers commonly supply protective caps on their hypodermic needles to insure that the needles are maintained in a sterile state for the use of health care workers, in injecting or withdrawing fluids and other substances into their patients bodies. Hypodermic needles and their protective caps are also supplied by manufactures to various researchers for the delivery or withdrawal of numerous substances. The protective needle caps primary purpose being to maintain the sterility of the needle before it is used by the researcher or health care worker.

Previous hypodermic syringe designs concentrated primarily on delivering the hypodermic needle in a usable sterile state so as not to infect the patient or intended recipient. They failed to protect the user from becoming infected after the needle has been contaminated by entry into the intended recipient's body, and show no thought in protecting the user from an accidentally, potentially fatal, contaminated needle strike.

This can clearly be seen by observing current procedures and product designs. For example: One major source of accidental needle strikes is caused by the extreme ease in which existing needle caps are designed to be removed from syringes. Because it is necessary for the user to be able to easily remove the needle cap from the syringe for use, needle caps are designed to be easily loosened. This makes them a prime candidate for being accidentally knocked off at a later time, due to their poor locking mechanisms. With the cap knocked off, the contaminated needle is exposed, thus endangering medical waste disposers and others to contaminated needle strikes. This can easily be demonstrated by simply dropping a hypodermic syringe with its cap reattached after use. In many cases the cap will come off, exposing the contaminated needle.

Probably the major source of needle strikes are caused by design induced procedures used with today's hypodermic syringes, for example: (1) The user is expected to grasp the protective needle cap between the fingers of one naked hand. (2) Remove the hypodermic syringe and its needle from the needle cap with the other hand. (3) Inject the needle into the subject, thus contaminating the needle. (4) Then withdraw the contaminated needle and replace it in the tiny aperture of the needle cap while it is held between the fingers of the users naked opposite hand. The bare fingers are exposed fractions of an inch from the contaminated needle, as this reinsertion procedure is done into the tiny aperture of the needle cap. The slightest miscalculation or upset can send the contaminated needle into the flesh of the exposed fingers or hand, thus infecting the user with possibly fatal virus, bacteria or other harmful substances. Stress, poor eyesight, being jarred, drug usage, distraction, bad lighting and numerous other causes can lead to a accidental needle stick, exposing the user and through secondary infections, possibly there family, friends, and others to disease or even death. In addition, extreme psychological stress can result to a user who has accidentally stuck himself with a contaminated needle, and is forced to wonder, sometimes indefinitely, whether he has contracted a fatal infection, since some test results are not conclusive.

With current trends in: bio-genetic engineering, chemical and biological development, and little understood new diseases, all rapidly increasing and all requiring hypodermic needle usage, it becomes imperative that the possibility of accidental contaminated needle strikes be minimized, to avoid infecting the workers in the above stated situations. This would help eliminate the possibility of incurable secondary infections spreading throughout society in epidemic proportions. Since it is well known that needle strikes or needle sticks as they are sometimes called, are a major work site accident in hospitals, laboratories, dentists' offices, and physicians' offices, it would be of great value to have a method and devices for replacement of a protective cap on the needle, which would keep the exposed extremities, especially the bare hands and fingers, a safe distance from the needle point. In addition, it would also be beneficial to have a method and device that would keep the needle cap in place so it couldn't be knocked loose when disposed. This invention describes a method or process and devices for handling existing hypodermic needle, needle cap and syringe in a safe manner, that could be very economically instituted using existing hypodermic needles, needle caps and syringes, thus minimizing the possibility of an accidental needle strike.

Several patents have been issued which claim to offer a solution to the needle strike problem, but serious limitations and drawbacks are present in all of them. For example: U.S. Pat. No. 4,596,562 (1986) to Vernon shows a device for handling syringe covers. Since needle cap outside diameters vary in size from manufacturer to manufacturer Vernon's reliance on a friction fit for the pre-drilled holes, would make the device impractical to use. Each device would have to match each manufactures outside needle cap diameter to obtain a functional friction fit. This would result in many different devices having to be carried around with the worker, with increased probability of confusing device or hole diameter with incorrect needle cap, resulting in accidents. Also, since it relies on a non controllable friction fit, the needle cap would likely be pulled back off the syringe exposing the needle if not very carefully removed from the device. In addition, the device would likely be costly to manufacture and would be easily misplaced in use, and as shown in Vernon's FIGS. 1-5, would not provide adequate distance from the fingers for safe usage. U.S. Pat. No. 4,654,034 (1987) to Masters et al. shows a specially designed safety needle cap. Unfortunately, this cap would have to be specially manufactured to the close tolerances of each manufactures syringe needle in order to maintain a friction fit as described, resulting in high construction costs and cooperation of the various needle manufactures. In addition, standard packaging and storage procedures would have to be changed, all at additional cost, to accommodate the non-standard shape of Masters' cap. Also, as shown and described in Masters, the diameter of the funnel and protective shield are much too small to afford significant protection. U.S. Pat. No. 4,717,386 to Simmons shows another safety device for a needle. It too relies on a friction fit of a pre-drilled hole which may be or may not work with varying needle cap diameters and designs. Simmons would also be subject to misplacement and inconvenience of use, since it must be transported with the worker at all times. In addition, it still places the user's fingers in close proximity to the re-inserted needle. U.S. Pat. No. 4,485,918 to Mayer shows a needle disposal apparatus. It relies on a large inconvenient to use funnel or box for needle recapping. Both are likely to be mislaid and must be transported from place to place and are subject to spillage if dropped. U.S. Pat. No. 4,664,259 to Landis shows a needle container and method for preventing accidental contact with a needle. It should be apparent that Landis would be costly to manufacture and would require radical changes in storage and shipping procedures. In addition, Landis operates with the needle cover still attached to the syringe with varying protrusions that could interfere with critical syringe needle placement in a patients vein, etc., which requires great accuracy in order to avoid missing the vein or target. All current procedures and hypodermic needle technology suffer from the following disadvantages:

(a) All hypodermic needle caps are designed to be held by bare hand only, forcing the user to operate the hypodermic needle in extreme close proximity to the exposed hand or fingers thereby maximizing the possibility of a needle strike into the hand or fingers.

(b) All hypodermic needles must be reinserted in the needle cap in extreme close proximity to the naked hand greatly increasing the probability of a needle strike.

(c) Redesigning of hypodermic needles and needle caps would be costly and would impact current disposal, shipping and storage procedures.

(d) Protective hand coverings or gloves would be costly to manufacture, inconvenient and/or uncomfortable to use, present problems with sterilization, be extremely inflexible by design in order to present enough strength to stop a needle puncture and would lack sensitivity so users could be hindered in emergency and other situations requiring normal hand feeling.

(e) Existing needles caps can be easily knocked off exposing their contaminated needle.

OBJECTS AND ADVANTAGES

Accordingly several objects and advantages of the present invention are:

(a) to provide a tool which removes the bare hand from the close proximity to the hypodermic needle thus minimizing needle strike possibility.

(b) to provide a method that allows the bare hand to control the needle cap in such a manner as to allow the reinsertion of a contaminated needle in the needle cap in a controlled manner, at a safe distance from the bare hand, which will drastically reduce the possibility of an accidental needle puncture.

(c) provide a method which would requires no redesigning of hypodermic needles and needle caps and utilizes existing procedures for disposal, shipping, and manufacturing of hypodermic needles and need caps.

(d) to provide a "bare handed" method of handling hypodermic needles and their protective caps that is convenient, fast, safe, easy and inexpensive to use and implement.

(e) to provide devices that would retain needle caps securely so they couldn't be easily knocked off yet could be removed easily for use.

(f) to provide devices to be used in the above method that could be easily and inexpensively installed by the manufacture, or in the field by the user if so desired.

(g) to provide devices to be used in the above method that could be inexpensively manufactured.

(h) to provide a method and devices that could help eliminate future epidemics caused or spread by secondary infections from needle stick victims.

DRAWING FIGURES 1-22

FIG. 11 shows a top view of an alternate embodiment with indented handle and syringe ring clamp.

FIG. 12 shows a side view of the embodiment of FIG. 11 as it is being assembled/disassembled on syringe.

FIG. 13 shows a top view of an alternate embodiment of needle cap holding device with female hole in handle and body clamping ring with male protrusion.

FIG. 14 shows a side view of the embodiment of FIG. 13 as it is being assembled/disassembled on the syringe.

Figure 1:
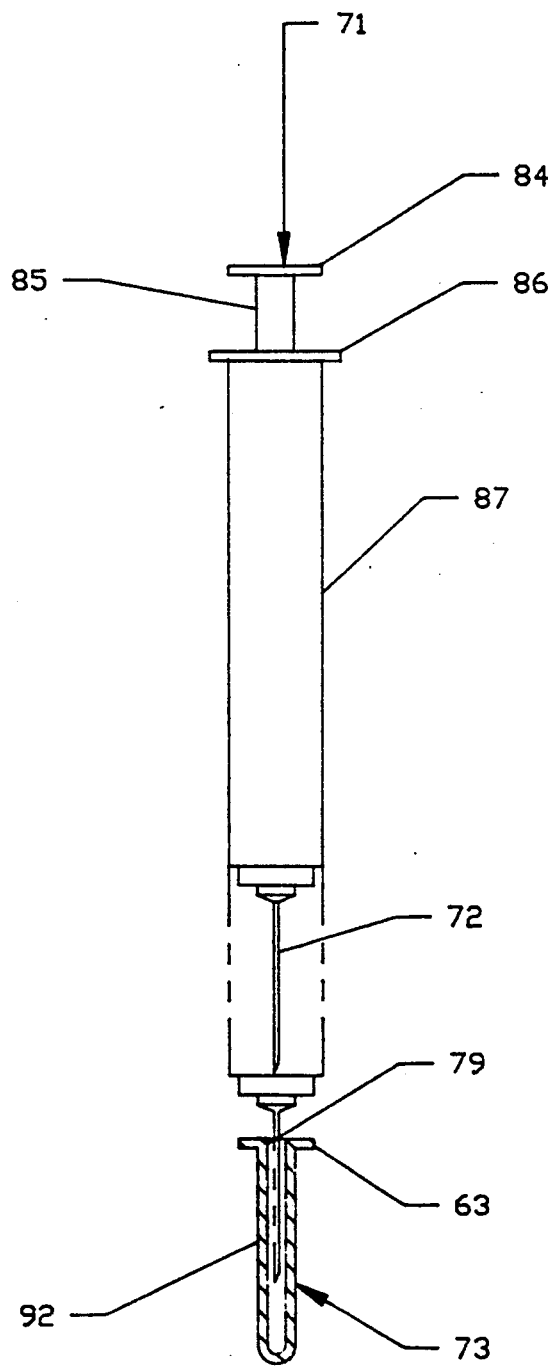
FIG. 1 shows a side view of a standard hypodermic syringe, needle and protective cap in use today.

REFERENCE NUMERALS IN DRAWINGS clamping device spring 25
loop 26
ridged loop 27
spring attachment 28
circular metallic washer 29
stamped teeth 30
concave side 31
cap holding tool 32
handle 33
gripping means control 34
shaft 35
tensioner 36
gripper 37
jaws 38
aperture 39
transmission means 40
gripping means 41
chain 42
recoiling device 43
clip 44
spring 45
spring housing 46
hole 47
pocket needle cap tool 48
handle 49
gripping means control 50
tubular container 51
internal transmission means 52
gripper 53
gripping loop 54
opening 55
ring 56
handle indent 57
syringe ring clamp 58
handle insert 59
female receptacle 60
body clamp 61
male protrusion 62
needle cap flange 63
hook 64
opening 65
cap 66
cavity 67
clip 68
loop aperture 69
alternate spring attachment 70
syringe 71
needle 72
needle cap 73
cap gripping end 74
handle attachment 75
handle 76
clamps 77
body 78
needle cap opening 79
holding device aperture 80
gripping apparatus 81
needle cap holding device 82
smooth gripping apparatus 83
plunger button 84
plunger neck 85
finger grips 86
syringe body 87
plunger clamping device 88
plunger end aperture 89
tab 90
ring attachment 91
needle cap barrel rim 92

DESCRIPTION—FIGS. 1-22

FIG. 1 shows a standard hypodermic syringe 71 in use today comprising: needle 72, and needle cap 73, the tiny aperture of the needle cap opening 79 where the needle 72 is inserted into the needle cap 73 thru needle cap opening 79, plunger button 84, plunger neck 85, finger grips 86, syringe body 87, and needle cap barrel rim 92. The opening 79 of the needle cap in most cases is less than ¼ inch and needle cap barrel rim 92 is designed to be held by the fingers during reinsertion of the needle 72 into needle cap opening 79 of needle cap 73. This puts the bare fingers and hand in extremely close proximity to the needle 72 as the reinsertion process is being done. It is no wonder that accidental needle sticks are such a prevalent work site accident, since users are forced to deal with such unforgiving close tolerances during needle 72 reinsertion into needle cap opening 79 of needle cap 73.

Figure 2:
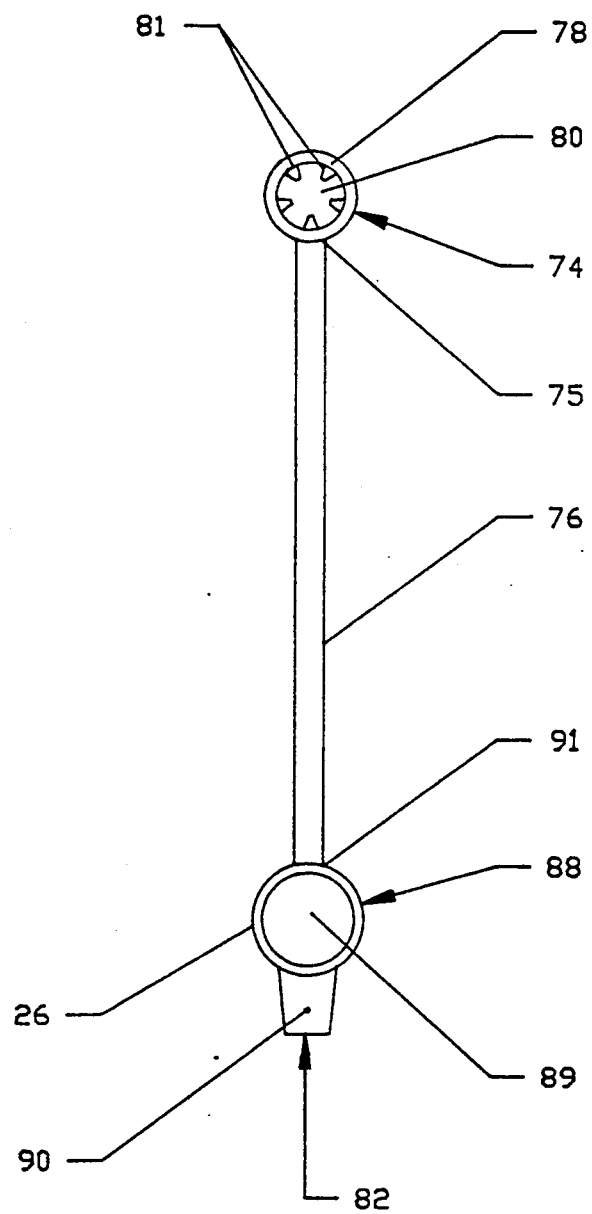
FIG. 2 shows a top view of the preferred embodiment of the needle holding device of this invention, with its needle cap gripping end at one end, and plunger clamping device at the opposite end of the handle.
Figure 4:
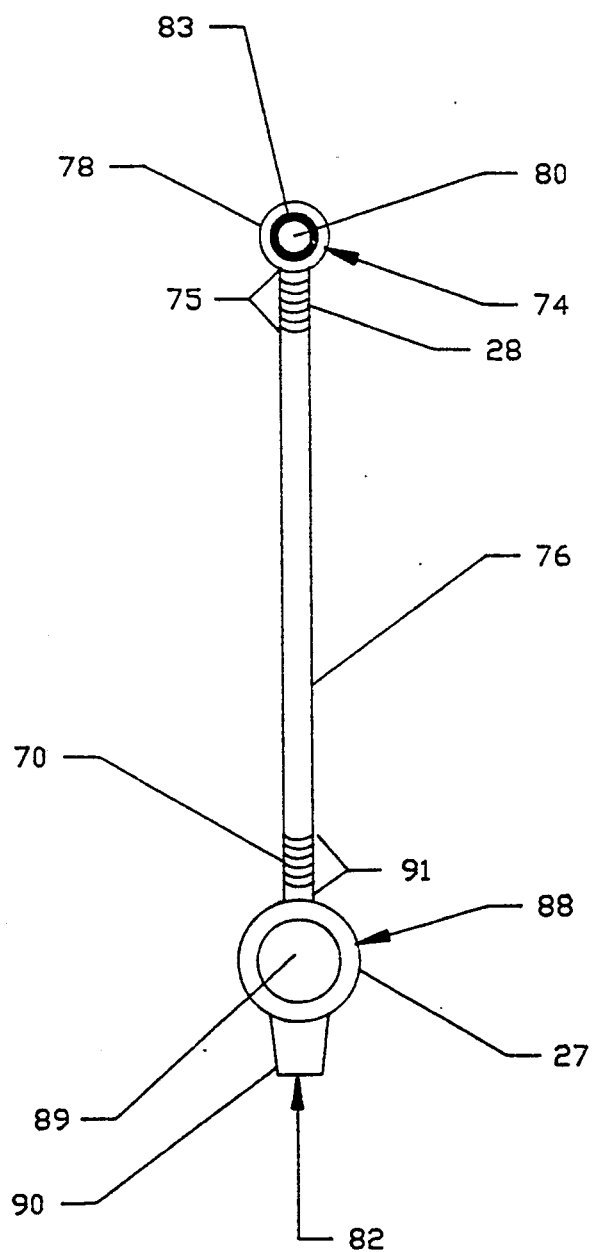
FIG. 4 shows a top view of an alternate embodiment with a spring connecting the handle to the cap gripping end.
Figure 5:
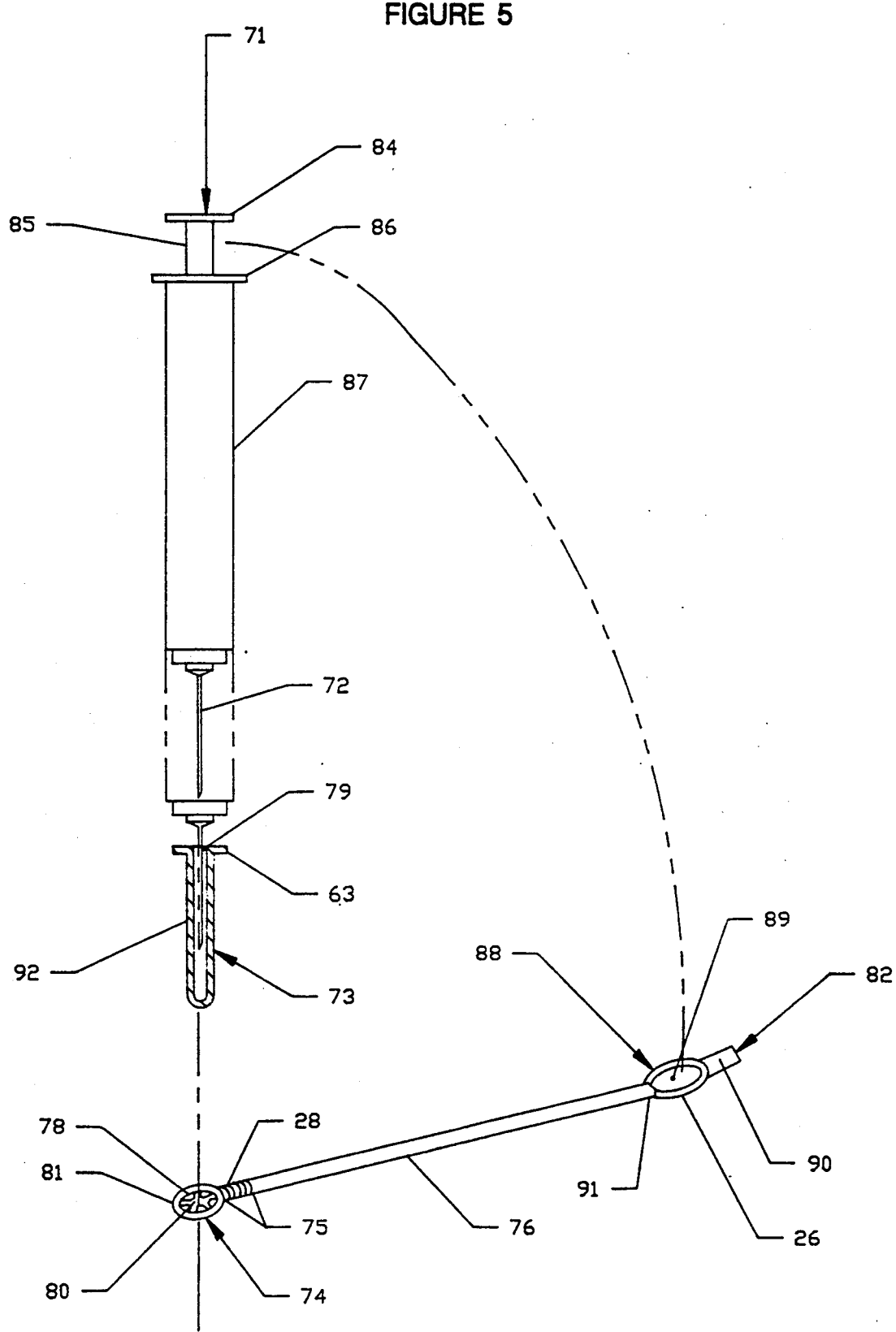
FIG. 5 shows a side view of the various components of the of preferred embodiment of the hypodermic syringe and needle cap holding device as they are being assembled/disassembled.

FIG. 2 shows the preferred embodiment of the needle cap holding device 82 comprising: cap gripping end 74, body 78, gripping apparatus 81, holding device aperture 80, handle 76, handle attachment 75, and plunger clamping device 88. Cap gripping end 74 is made comprising gripping apparatus 81, and holding device aperture 80. Cap gripping end 74 is attached to handle 76 by handle attachment 75. Plunger clamping device 88 is attached to handle 76 by ring attachment 91. As shown in FIG. 5, cap gripping end 74 is designed to allow needle cap 73, to be inserted into holding device aperture 80 with the needle cap 73 being held in place by a gripping apparatus 81. As shown in FIGS. 2 and 5, cap gripping end 74 and/or body 78 can comprise any suitable material singly or in combination, that would allow retention and or formation of gripping apparatus 81 or its alternate embodiment, smooth gripping apparatus 83 (shown in FIGS. 3 and 4). Some possible materials are; metals, alloys, nylons, plastics, woods, rubbers or any other suitable materials which would provide sufficient support for the gripping apparatus 81 or smooth gripping apparatus 83, and the needle cap 73. Cap gripping end 74 can be made comprising the same materials as comprises the gripping apparatus 81, or differing materials as comprises gripping apparatus 81. Cap gripping end 74 comprising; body 78, gripping apparatus 81, with holding device aperture 80 can be stamped or molded out of one material. Alternately, cap gripping end 74, gripping apparatus 81 with holding device aperture 80, can be made comprising differing materials. Cap gripping apparatus 81 can be attached to cap gripping end 74 by any one or a combination of processes such as: lamination, fusion, molding, press fit, screwed, keying, machining, or any other process allowing retention of cap gripping apparatus 81 in cap gripping end 74. All the above stated facts concerning cap gripping apparatus 81 can be applied to alternate embodiment, smooth gripping apparatus 83 and visa versa.

Figure 17:
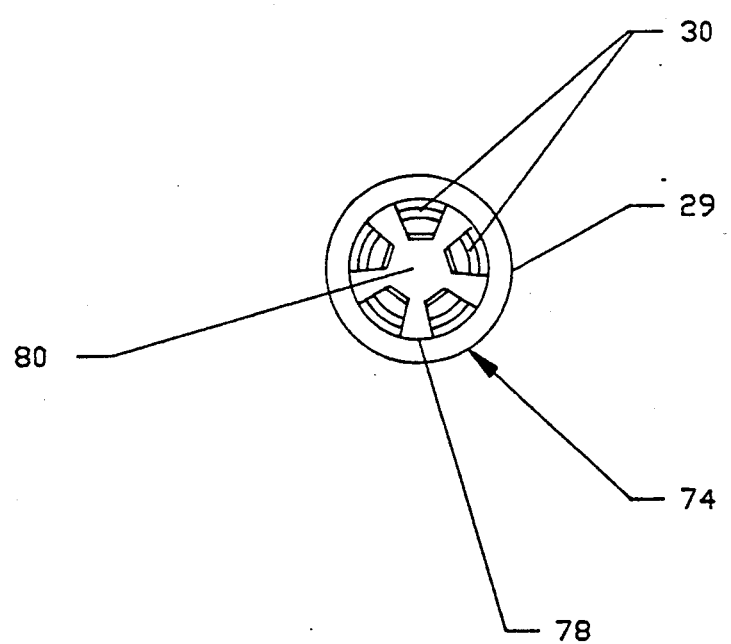
FIG. 17 shows a top view of cap gripping end, as viewed looking down into concave teeth aperture.
Figure 18:
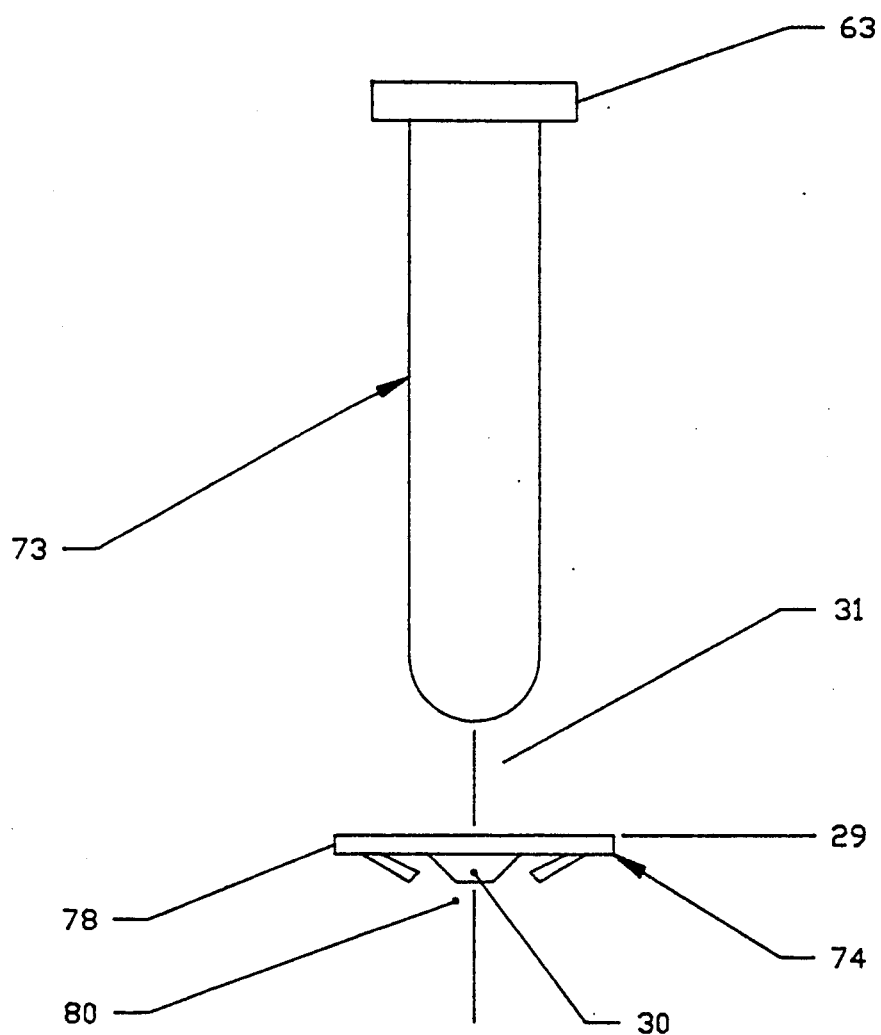
FIG. 18 shows a side view of the embodiment cap gripping end with needle cap being inserted.

As shown in FIG. 17 top view, one embodiment of the cap gripping end 74 comprises a body 78, a circular metallic washer 29 with stamped teeth 30, leading to the holding device aperture 80 with stamped teeth 30 forming a concave hole for holding device aperture 80 as shown in FIG. 18 side view and FIG. 17 top view. This will allow needle cap 73 closed end first, to be inserted into said aperture 80 thru concave side 31, but will not allow withdrawal of said needle cap from concave side 31. The preferred embodiment (FIG. 2) has the same shape as in FIGS. 17 and 18, but instead utilizes a nylon/plastic composite similar to the material used in the cinch straps commonly called "ty-rap", to form the washer 29 comprising body 78, concave aperture 80 with stamped teeth 30 as described above. Different materials and or variations of the shapes of FIGS. 17 and 18 could be possible, as the description and drawings are not meant to be limiting the scope of the invention in any manner.

As shown in the preferred embodiment of FIG. 2, the gripping apparatus 81 are a set of teeth or nubs that allow the needle cap 73 to be inserted in aperture 80 and grip onto the needle cap 73 securely holding it in place in the cap gripping end 74. The gripping apparatus 81 can also be made comprising one of, or a combination of various surface irregularities such as: serrations, points, indentations, ridges, striations, or any other deviation or disruption of a smooth surface that would cause a gripping action on needle cap 73. The gripping apparatus 81 can also comprise a deviation, variation or disruption of a circular aperture which would cause a gripping or holding action on needle cap 73.

Figure 3:
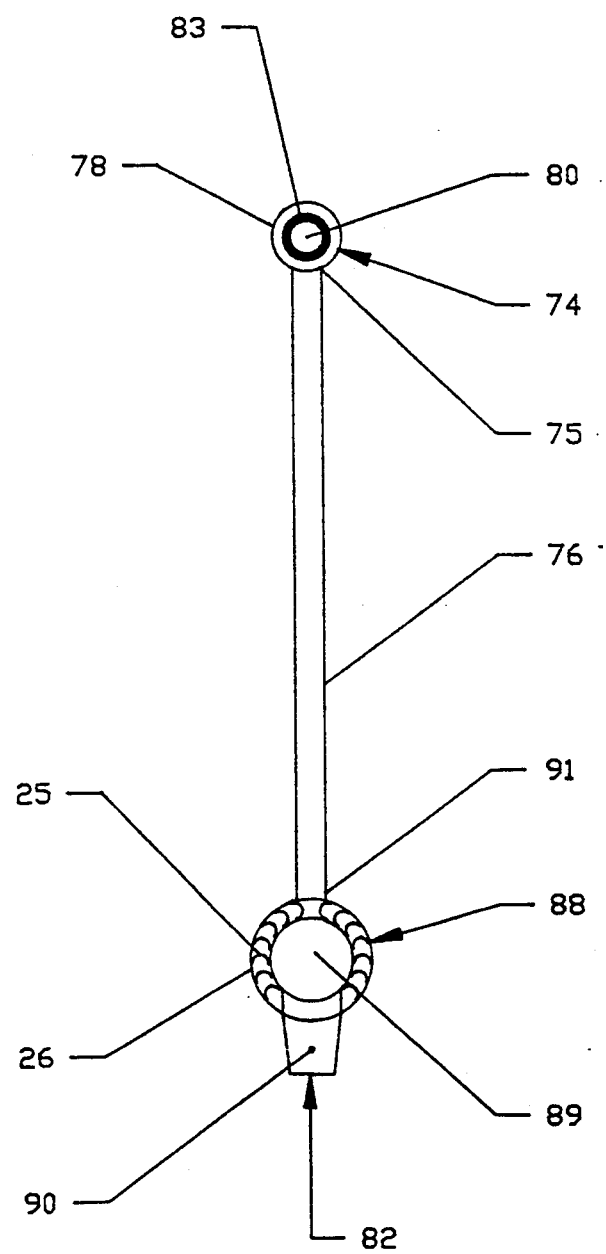
FIG. 3 shows a top view of an alternate embodiment with clamping device comprising a spring and gripping end comprising a smooth aperture.

FIG. 3 shows another embodiment with a smooth gripping apparatus 83 illustrated. The smooth gripping apparatus 83 can comprise rubber or other suitable substance that would allow a snug fit and form holding force on the needle cap 73. The smooth gripping apparatus 83 can be made comprising a smooth gripping surface with no teeth or numbs. Or in an alternate embodiment, made comprising a smooth surface and various irregularities on or within said smooth surface that would form a tight frictional fit with the outside surface of needle cap 73 and the surface of smooth gripping apparatus 83. Or in another embodiment, glue or other gripping substance of a suitable kind, or a lamination process can be used to retain the needle cap 73 and the cap gripping end 74 together. Cap gripping end 74 can also be designed so that it is easily removably from needle cap 73 by eliminating any gripping apparatus 81 or apparatus 83 (FIGS. 2–5), and instead providing a smooth wall around the aperture 80 (not shown). This would allow the needle cap holding device 82 to be removed from the needle cap 73 and reused. If locking of the needle cap 73 were desired in the last described embodiment, cap gripping end 74 can be inserted on needle cap 73 and a locking device attached around needle cap barrel rim 92 wedging or retaining cap gripping end 74 in place on needle cap barrel 24 (not shown). Cap gripping end 74 can also be designed with jaws or with a belting or strapping method (not shown) which would allow a wrap around method of attaching cap gripping end 74 to needle cap 73 thus eliminating the insertion method of installing the needle cap 73 into cap gripping end 74. Cap gripping end 74 can also be designed by using closeable or restricting aperture (not shown).

As shown in FIG. 2, cap gripping end 74 is attached to handle 76 by handle attachment 75. Handle attachment 75 can be at end of handle 76 and the edge or rim of cap gripping end 74 as in the preferred embodiment shown, or at other positions on the handle 76 and/or cap gripping end 74 (not illustrated). Handle attachment 75 can be molded or attached directly to cap gripping end 74 with a flexible material that will allow it to be bent for extension or retraction. Handle attachment 75 can also be molded as a continuous part of cap gripping end 74 as in the preferred embodiment of FIG. 2, or attached to cap gripping end 74 using a resilient material which would allow bending of the handle attachment point 75 and allow it to bounce back to its or original horizontal or flat position. The preferred embodiment of FIG. 2 uses the nylon/plastic composite usually found in the cinch straps commonly known by those skilled in the art as "Tie-raps", which are used to hold bundles of electrical wiring and/or other objects in place. Handle attachment 75 can also be made as a conventional pinned hinge (not shown) or any other hinging or pivoting material or device which can be bent to form an angle and could be returned to its original flat for horizontal position. This would allow handle 76 to be pivoted or moved from the horizontal (FIG. 7) to the vertical (FIG. 6) and back to the horizontal (FIG. 7) in relation to cap gripping end 74. Handle attachment 75 could also be made comprising a spring or other spring like device as in FIG. 5 shown as attachment 28.

Figure 6:
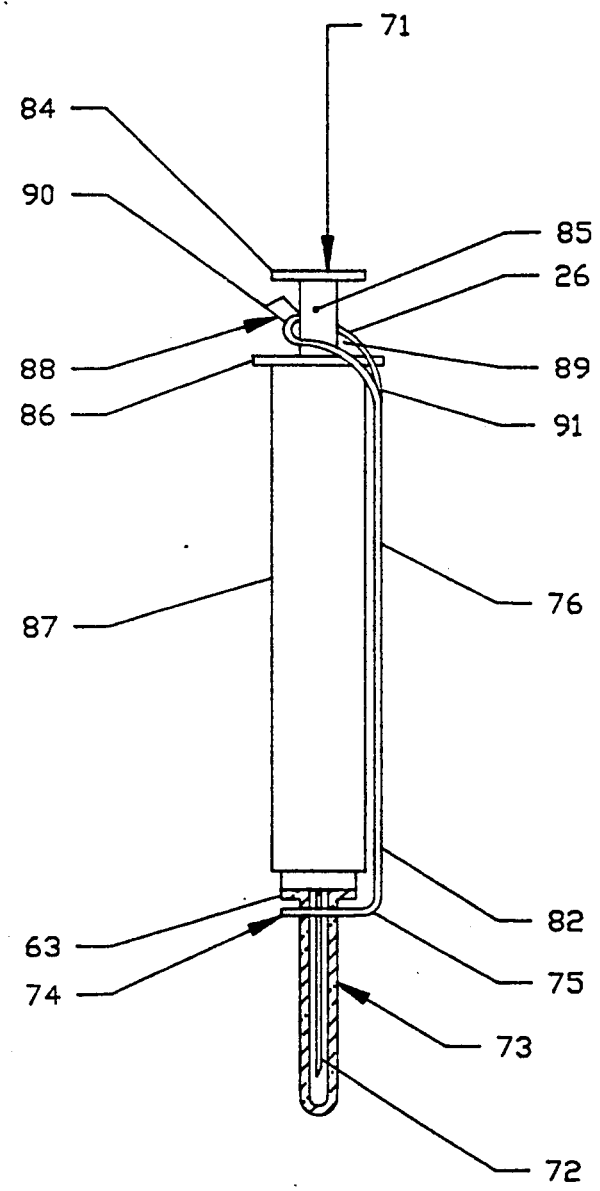
FIG. 6 shows a side view of the preferred embodiment of the hypodermic syringe with a needle cap on and needle cap holding device installed on needle cap and secured to syringe around syringe neck.

Plunger clamping device 88 is attached or molded to handle 76. FIG. 2 shows a top view of the preferred embodiment of this invention. Cap gripping end 74 is attached to handle 76 at handle attachment 75. Plunger clamping device 88 is attached to handle 76 sufficient distance from cap gripping end 74 to allow plunger clamping device 88 to be attached to plunger neck 85 when cap gripping end 74 is installed on needle cap 73 and needle cap 73 is installed on syringe 71 as shown in FIG. 6. Plunger clamping device 88 shown in FIG. 2, comprises: ring attachment 91, loop 26, tab 90, aperture 89. Plunger clamping device 88 can be attached anywhere along the handle 76 or at the very end of the handle 76 as shown in the preferred embodiment of FIG. 2.

FIG. 11 shows a top view of an alternate embodiment of plunger clamping device 88 comprising and indented handle 57 and a syringe ring clamp 58. Syringe ring clamp 58 (FIG. 12) is slide up syringe body forming a tight frictional fit or it can be laminated to, or molded from syringe body 87. Syringe ring clamp 58 can be allowed to move on syringe body 87 is desired. FIG. 11 shows handle insert 59. Handle indent 57 is designed to be inserted and secured in handle insert 59 when syringe ring clamp 58 is installed on syringe body 87 and handle 76 is in its retracted position along syringe body 87. Any type or attachment device or form can be used to make syringe ring clamp 58, handle insert 59, and handle indent 57. One alternate design is shown in FIG. 13 as body clamp 61 with male protrusion 62 and handle 76 with female hole 60. Male protrusion 62 is designed to penetrate female receptacle 60 and securely lock in place handle 76. FIG. 14 shows this embodiment being assembled/disassembled on the syringe 71. Body clamp 61 can be allowed to move on syringe body 87 and alternately can be fixed or a part of syringe body 87 in other embodiments (not shown).

Figure 15:
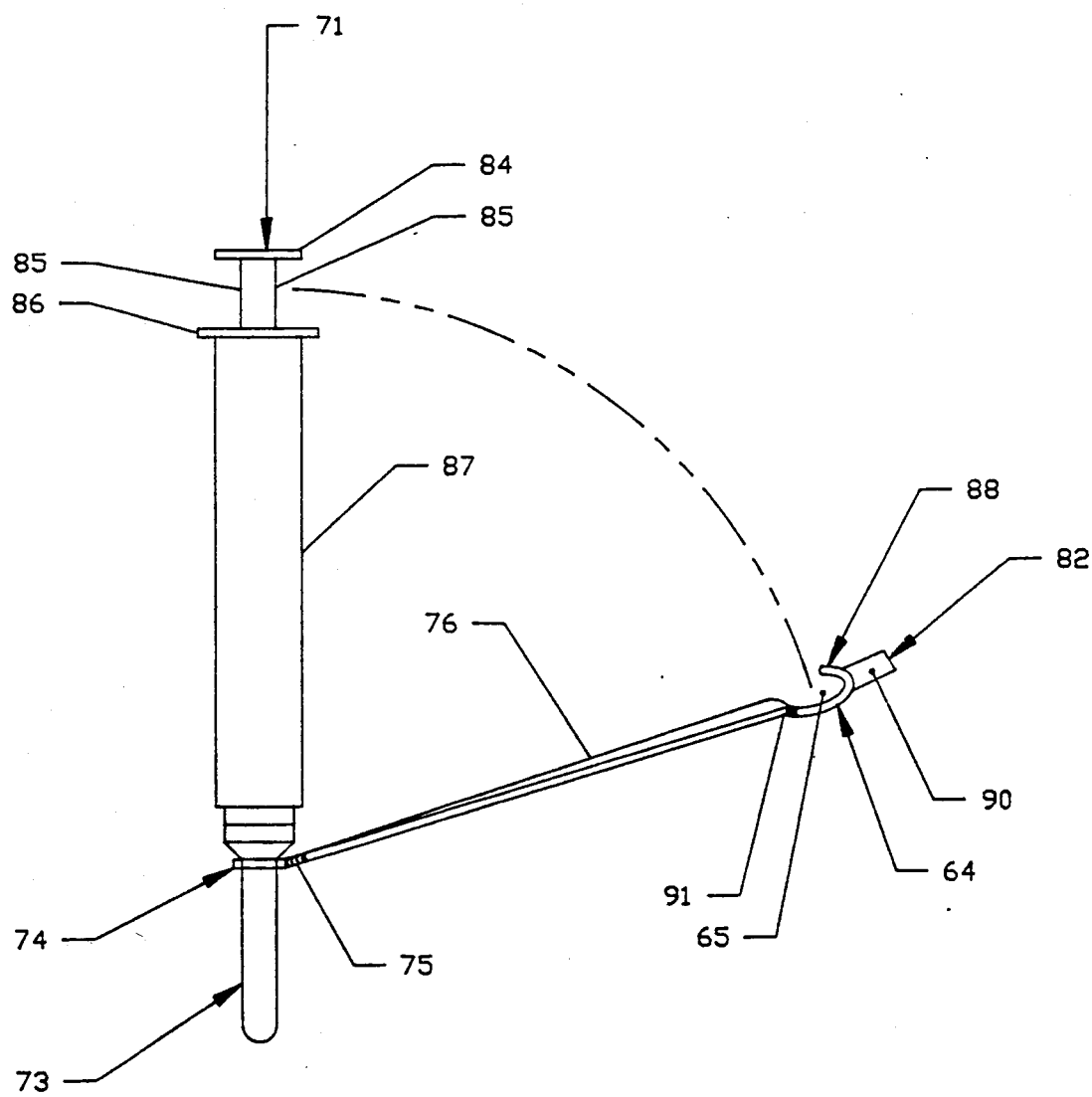
FIG. 15 shows a side view of an alternate embodiment with a hook for a clamping device.

FIG. 15 shows an alternate hooking embodiment of plunger clamping device 88 comprising hook 64, opening 65, ring attachment 91, and tab 90. Hook 64 in the preferred embodiment shown, clamps around plunger neck 85 by using opening 65. Ring attachment 91 provides the flexibility for this to be easily done. In an alternate embodiment (not shown) hook 64 can be designed to attach over finger grips 86 or around plunger body 87 or around plunger neck 85 and over finger grips 86 or any combination of the above. In still another embodiment, hook 64 can be a plurality of hooks. The shape or hook 64 can vary as necessary.

Figure 16:
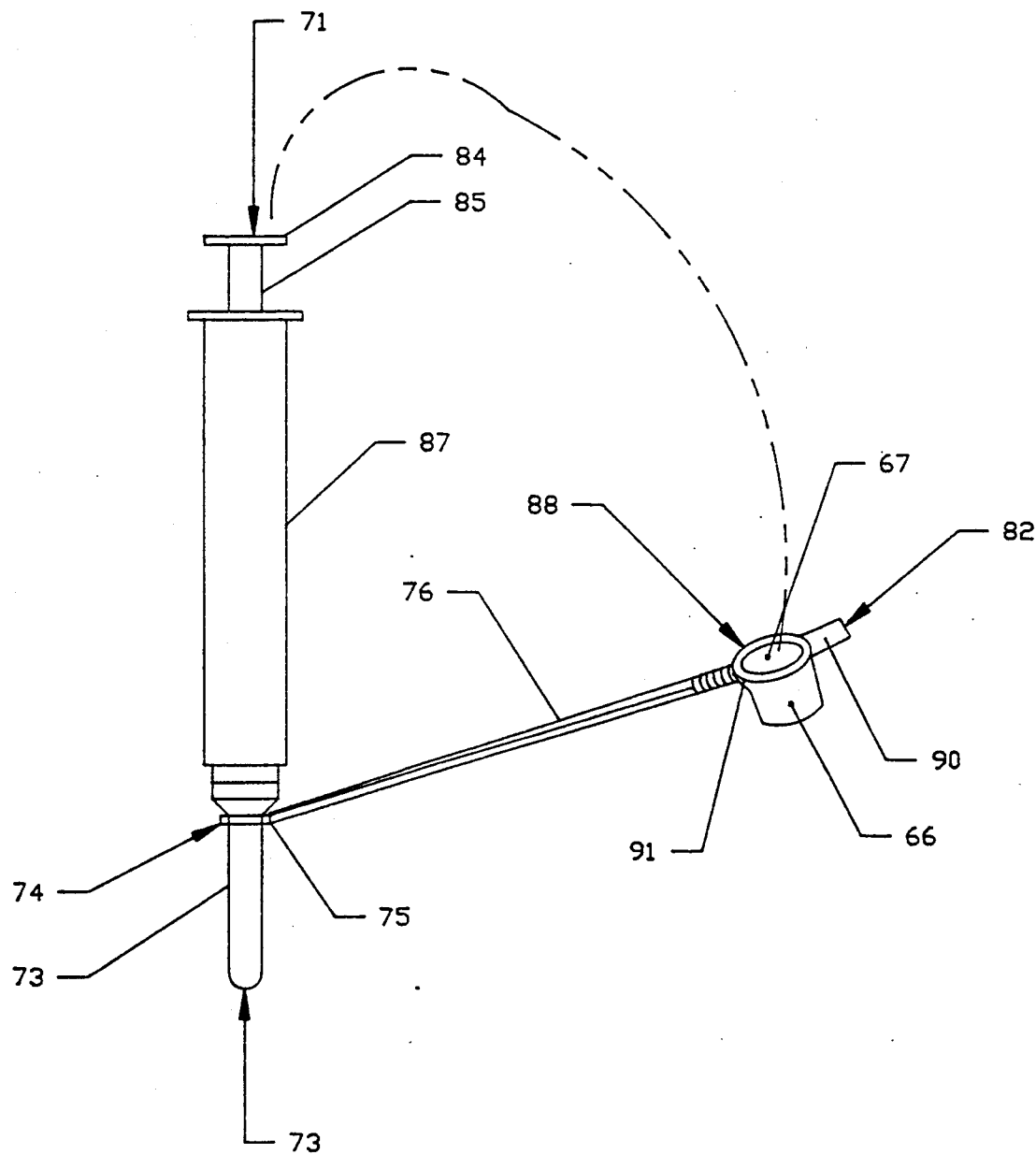
FIG. 16 shows an alternate embodiment with a cap as the the clamping device.

FIG. 16 shows a capping embodiment or plunger clamping device 88 comprising; cavity 67, cap 66, tab 90, and ring attachment 91. Cap 66 in the preferred embodiment shown pulls over plunger button 84 and caps down over it in a secure manner. Ring attachment 91 provides the flexibility for this to be easily accomplished.

Plunger clamping device 88 can be a pair of resilient clips or clamps (shown in FIG. 9 as clamps 77) that would allow handle 76 to be secured to syringe body 87 (FIG. 10) or plunger neck 85 or around or over plunger button 84 depending on the location plunger clamping device 88 is connected to handle 76. The clamps 77 would have the disadvantage of being able to be slide down the syringe body 87 if attached as in FIG. 10 possibly exposing the needle 72. This can be corrected by putting a retainer or ridge or other securing device on syringe body 87 which would serve as an abutment or restriction to clamps 77 downward travel on syringe body 87. FIG. 10 shows ring 56 which serves the abutment purpose described above. Ring 56 can be tightly press fit ring, which can also be laminated or a wrap around design can be used.

In the preferred embodiment of FIG. 2, plunger clamping device 88 comprises and elastic loop 26. Plunger clamping device 88 can also be made of material capable of being bent with non-resilient characteristics so the user can bend plunger clamping device 88 around one of the components of syringe 71 forming a snug fit or secure connection. Plunger clamping device 88 can consist of various materials in combination or singly such as; sticky substances, velcro strips, adhesive tape, rubber, plastic or other suitable materials. Plunger clamping device 88 can be made comprising said materials singly or in combination. Plunger clamping device 88 can be made comprising various shapes singly or in combination such as: wrap around, belt like with cinch, half wrap around, loop, cap like or hook like. Plunger clamping device 88 can take various positions on the handle 76 including but not limited to: the vary end of handle 76. Plunger clamping device 88 can fasten in various positions on syringe 71 (refer to FIG. 1) such as: on syringe body 87, on plunger neck 85, plunger button 84, on finger grips 86, over plunger button 84, over plunger button 84 in a capping form, over plunger button 84 and around plunger neck 85 in a loop form, attached or around finger grips 86 in any manner as well as other positions.

Shown in FIG. 6, plunger clamping device 88 has aperture 89, capable of passing over plunger button 84 and around plunger neck 85. Plunger clamping device 20 can be made consisting single or in combination with any of the following materials: rubber, elastic, rubber band, plastic, vinyl, a spring, or any other material or device which can be stretched and will snap back in place so that the aperture 89 can be enlarged to slip over plunger button 84 and would contract or constrict around plunger neck 85. In the preferred embodiment of FIG. 2, plunger clamping device 88 comprises a rubber like substance in loop 26 that can be stretched to enlarge aperture 89 and will snap back to original form when released. Plunger clamping device 88 can comprise said materials singly or in combination and is not limited to only said materials. Alternately, plunger clamping device 88 (as shown in FIG. 4) can be made of flexible or a rigid material with a suitable size plunger end aperture 89 to allow placement over plunger button 84, said aperture 89 of plunger clamping device 88 not needing to be resilient. In this embodiment some sort of elastic, or spring, or spring like substance, or device single or in combination, can be provided somewhere between cap gripping end 74, and plunger clamping device 88. As shown in the embodiment of FIG. 4, a spring attachment 28 is used between handle 76 and cap gripping end 74. Clamping device 88 can be in the form of a cap that would fit over plunger button 84 with cavity 67 and cap 66 as shown in FIG. 16. Plunger clamping device 88 can be in the form of a hook 64 with opening 65 as shown in FIG. 15.

In FIG. 2 loop 26 can be made consisting singly or in combination with any of the following materials: rubber, elastic, rubber band, plastic, vinyl, a spring, or any other material or device which can be stretched and will snap back in place so that the aperture 89 can be enlarged to slip over plunger button 84 and would contract or constrict around plunger neck 85. Loop 26 can also be made comprising said materials singly or in combination. In the preferred embodiment shown in FIG. 2, loop 26 is comprised of a elastic rubbery substance which will allow the user to stretch clamping device 88 over plunger button 84 and secure around said plunger neck 85 as shown in FIG. 6. One suitable substance or material for loop 26 wound be the rubber used in the common rubber band, but by no means is this the only suitable substance. In an alternate embodiment shown in FIG. 3, plunger clamping device 88 comprises a spring described as clamping device spring 25. Many different types of springs can be used, provided they can be connected to handle 76. Spring material for spring 25 can consist singly or in combination of: spring steel, plastic, rubber, elastic, and or any other material or device that would be expandable and would return to shape when released. Material for spring 25 can comprise said materials single or in combination but is not limited only to the use of said materials. Clamping device spring 25 can comprise many forms including but not limited to; full spring forming loop attached to handle 76, partial spring contained in loop attached to handle 76, spring forming connected between loop 26 and handle 76, and even a spring forming connection between cap gripping end 74 and handle 76. In the embodiment shown in FIG. 3 clamping device spring 25 is a full spring forming a loop attached to handle 76 by ring attachment 91.

Ring attachment 91 as shown in FIGS. 2–8, attaches plunger clamping device 88 to handle 76. Ring attachment 91 can be at the edge or rim of plunger clamping device 88 as shown in the preferred embodiment of FIG. 2, or at other positions on the handle 76 and/or plunger clamping device 88 (not illustrated). Ring attachment 91 can be molded or attached directly to plunger clamping device 88 and handle 76. Ring attachment 91 can also be molded as a continuous part of plunger clamping device 88 and/or handle 76. Ring attachment 91 can be a lamination or fusion or any other process or device, that would connect handle 76 to plunger clamping device 88. Ring attachment 91 can be in the form of a spring as shown in FIG. 4 as alternate spring attachment 70. In the preferred embodiment of FIG. 2, ring attachment 91 is molded or laminated to handle 76 of plunger clamping device 88 comprising a elastic/rubbery material.

FIG. 2 of the preferred embodiment shows a tab 90 attached to loop 26 of clamping device 88. Tab 90 is provided to allow the user a holding point to more easily stretch clamping device 88 over plunger button 84 for installation on plunger neck 85 or conversely, for removal. Tab 90 can be attached anywhere on or around loop 26 that will allow convenient use. In the preferred embodiment it is attached to the end of loop 26 but can be attached elsewhere on or around loop 26. In the embodiment of FIG. 3, tab 90 is attached to clamping device spring 25 as shown, but can be attached anywhere on or around clamping device spring 25. In the embodiment of FIG. 4, tab 90 is attached to ridged loop 27 as shown, but can be attached anywhere on or around ridged loop 27. Tab 90 can be absent in all embodiments if desired. Tab 90 can be hinged so that it can be folded or it can designed to be movable. Tab 90 can be attached at different and angles to plunger clamping device 88. Tab 90 can be made of any material that would allow a holding or pulling force to be applied to it. Tab 90 can take numerous shapes suitable for finger holding or gripping. In the preferred embodiment of FIG. 2 tab 90, is molded out of the same elastic material as comprises loop 26. In the alternate embodiment of FIG. 3, tab 90 is attached to clamping device spring 25 by a wrap round laminating method and consists of a plastic/nylon material.

FIG. 4 shows an alternate embodiment of the invention in which spring attachment 28 connects needle cap gripping end 74 to handle 76, and handle 76 is attached to ridged loop 27. Spring attachment 28 can also be located any other position on the handle 76, including but not limited to, at the position of ring attachment 91 as indicated by alternate spring attachment 70 shown in FIG. 4. In still another embodiment (not shown), spring attachment 28 can be located at multiple positions on handle 76, including handle attachment 75 and ring attachment 91 simultaneously. In yet another embodiment, the entire handle 76 can be comprised of a spring. The said spring can comprise any material that would exhibit resilient spring like characteristic. FIG. 4 shows ridged loop 27. Aperture 21 of ridged loop 27 is of sufficient size to allow it to be placed over plunger button 84 and around plunger neck 85. Ridged loop can consist of any material that will support an aperture of said size.

Figure 8:
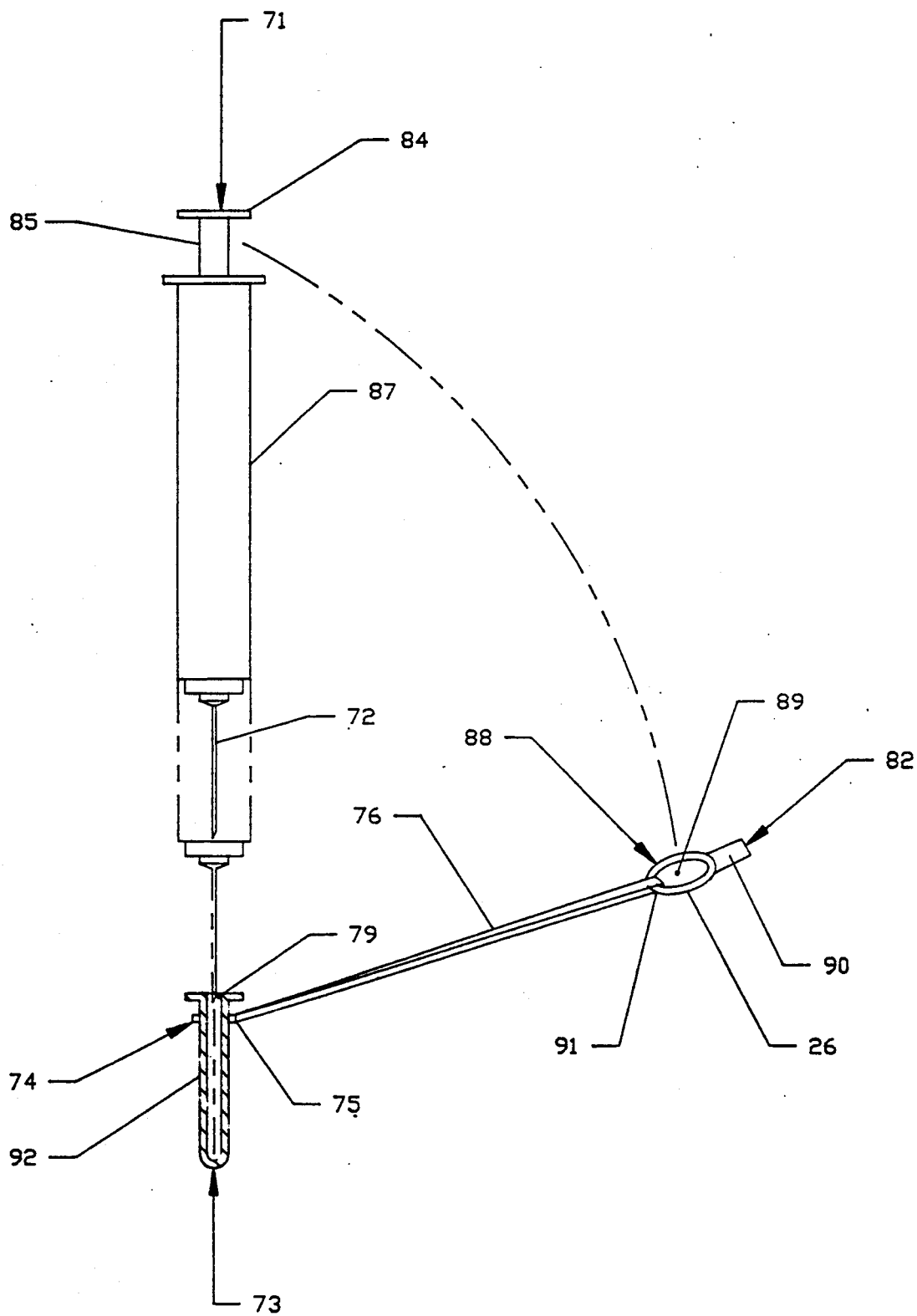
FIG. 8 shows a side view of the preferred embodiment shown in FIG. 2 with the needle being inserted/removed and handle extended for holding.

FIG. 8 shows a side view of the preferred embodiment of FIG. 2 needle cap holding device 82 installed on a conventional needle cap 73 with handle 76 extended, so the user can hold needle cap 73 a safe distance from the hand by handle 76, as needle 72 is reinserted into needle cap opening 79.

It is important to note that needle cap holding device 82 and all its components can be made from one material and formed by molding, stamping, or any other process that would allow construction of needle cap holding device 82. Alternately, needle cap holding device 82 can be made of differing materials, and or mixtures of materials. Needle cap holding device 82 can be comprised of varying materials and internal and or external stiffeners and or braces. Needle cap holding device 82 can be formed or constructed using differing processes of assembling the individual components. In addition, different embodiments described in the specification and drawings, and their components, may be freely intermixed to form new embodiments of the invention and in no way are the illustrations and specification to be constructed as limiting the scope of this invention.

Figure 19:
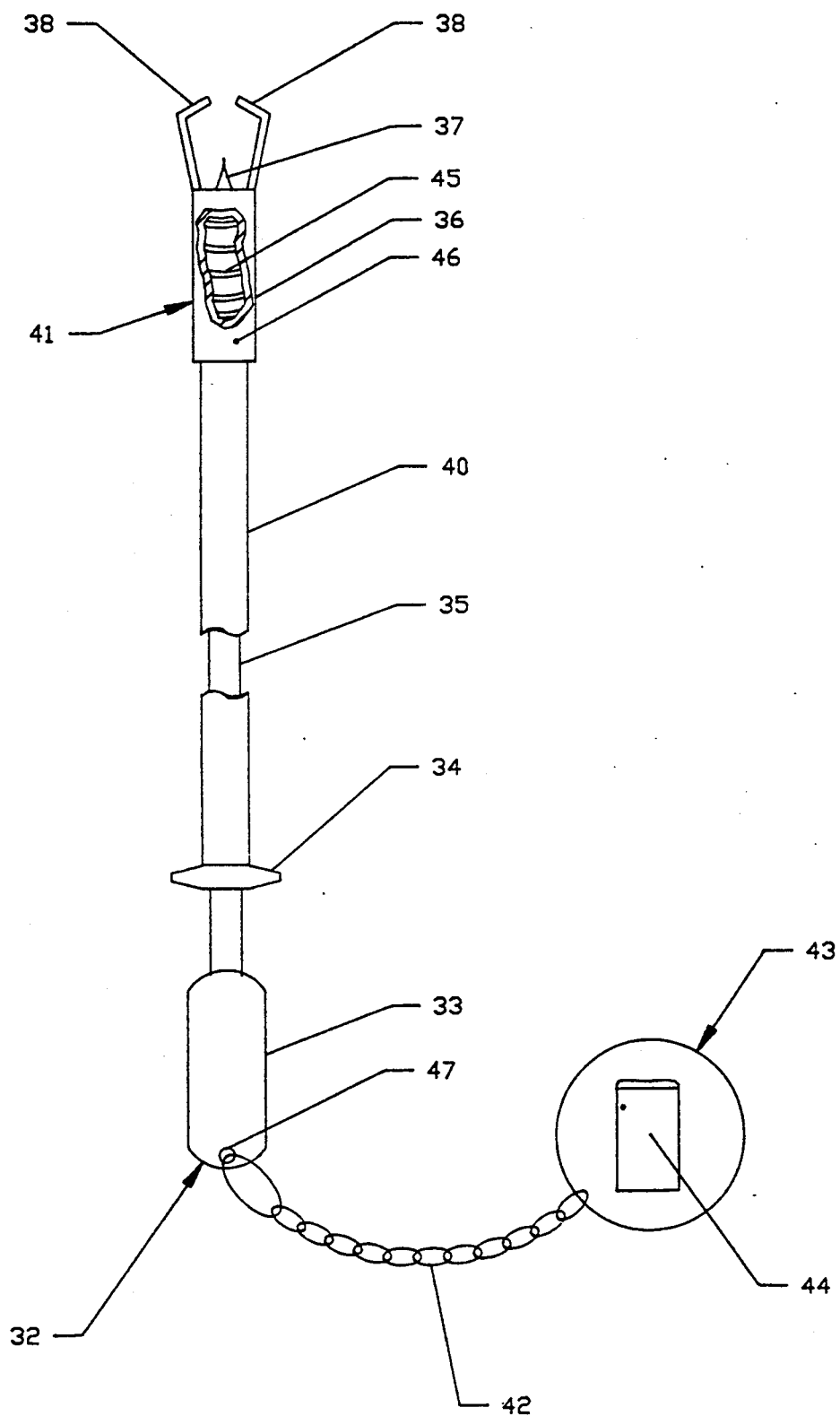
FIG. 19 shows a top view of the needle cap holding tool attached by chain to a recoiling device.

Another embodiment of the invention is shown in FIG. 19 as cap holding tool 32. This embodiment is used as a tool which can be carried with the worker and reused. Cap holding tool 32 comprises a handle 33, gripping means control 34, shaft 35, tensioner 36, gripper 37, jaws 38, aperture 39, transmission means 40, and gripping means 41. Handle 33 is attached to or molded or stamped from shaft 35. Handle 33 can be made of any material that would provide a suitable holding surface. Handle 35 can also be made of the same material or different material as comprises shaft 35. Handle 35 can take many forms including but not limited to, an extension of the form of shaft 35. In the preferred embodiment shown in FIG. 19, handle 33 is comprised of plastic, and a hole is provided to allow shaft 35 to be inserted in handle 33 and laminated or press fit in place.

Shaft 35 in the preferred embodiment (shown in FIG. 19) is attached to handle 33 on one end and gripping means 41 on the other end. Shaft 35 can be made in a solid form. Shaft 35 can also comprise a hollow or tubular from or any other form that would allow transmission means 40 to be operational in combination or singly, in, or around, or through shaft 35. Shaft 35 can comprise any material or combination of materials suitable for support of the components of cap holding tool 32. In the preferred embodiment shown, shaft 35 is a solid steel shaft.

Figure 20:
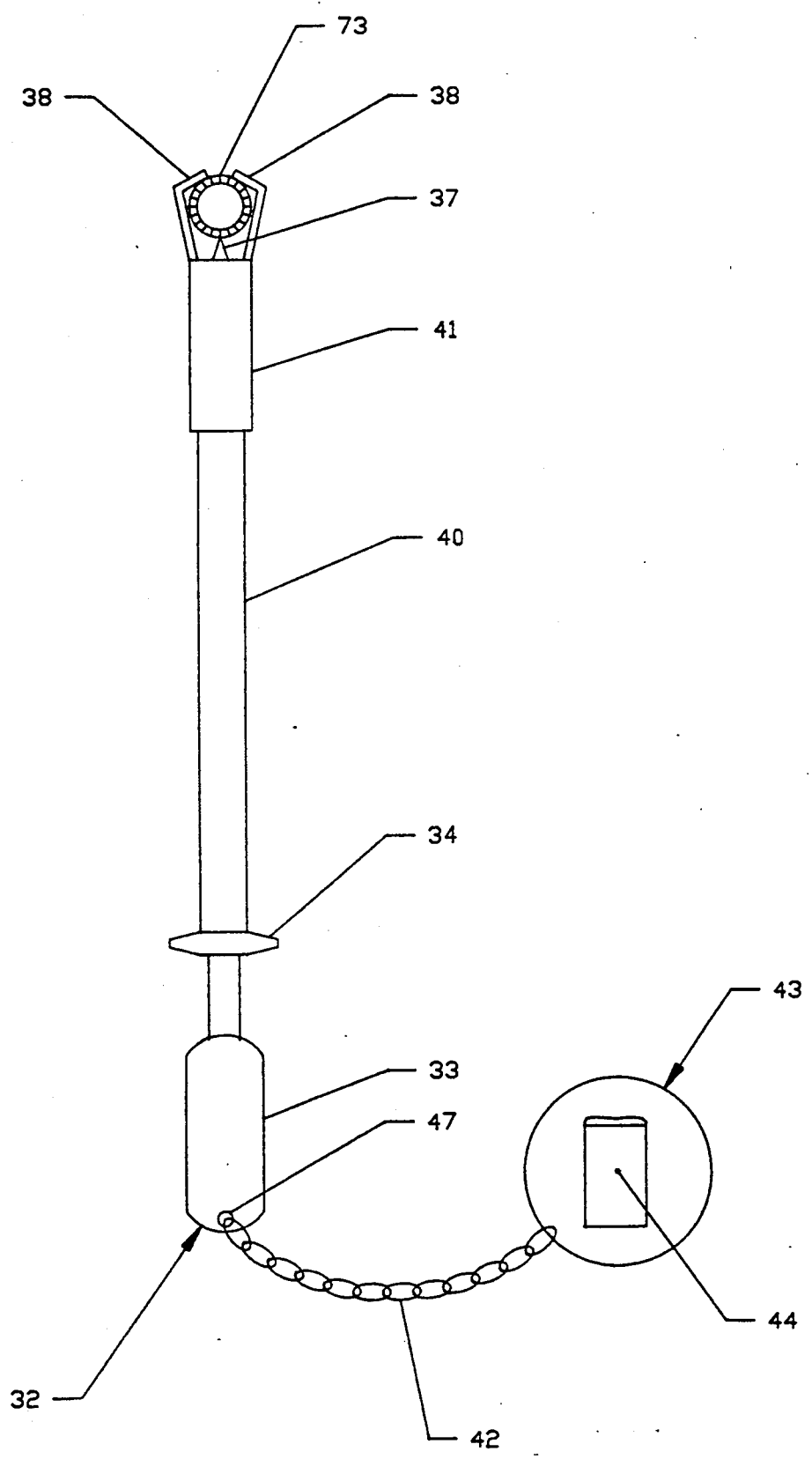
FIG. 20 shows a top view of the embodiment of FIG. 19 with needle cap inserted in jaws.

Transmission means 40 (shown if FIG. 19) transfers force from gripping means control 34 to gripping means 41. Transmission means 40 can comprise any mechanism or device that would allow gripping means 41 to be operated by manipulation of gripping means control 34. Gripping means control 34 can be attached to transmission means 40 in any manner and in any form that will allow the user to manipulate gripping means control 34 from handle 33. Transmission means 40 can be attached to, or contained in cap holding tool in any manner that will allow the user to control the operation of gripping means 41 while holding handle 33. In the preferred embodiment shown, transmission means 40 consists of a hollow tube that is around shaft 35 and allows transmission means 40 to be slide back and forth on shaft 35 transferring force to gripping means 41 from gripping means control 34 causing jaws 38, to be moved away from gripper 37, thus enlarging aperture 39, when gripping means control 34 is pushed in a direction away from handle 33. When the force is removed from gripping means control 34, jaws 38 retract back to their original position thereby gripping needle cap 73 inserted as shown in FIG. 20. In another embodiment, a locking device can be installed so jaw 38 would not automatically retract when said force is released. In the preferred embodiment shown (FIG. 19), gripping means control 34 is attached to transmission means 40 in the vicinity of handle 33 so the user can manipulate gripping control 34 from handle 33. In the preferred embodiment shown, transmission means 40 is a hollow tube comprised of plastic and nylon. Gripping means control 34 is attached to transmission means 40. Gripping means control 34 is a plastic button with a hole in the center, said hole containing an aperture large enough to allow shaft 35 to be slid through it.

Transmission means 40 can be connected to gripping means 41 in any manner that will allow gripping means 41 to be manipulated from the vicinity of handle 33. In FIG. 19 of the preferred embodiment, transmission means 40 is attached to gripping means 41 by tensioner 36. Tensioner 36 can comprise any device or mechanism that allows a continuous force to be applied to jaws 38 and or gripper 37 when needle cap 73 is inserted in aperture 39 (FIG. 20). In the preferred embodiment shown, tensioner 36 contains a spring 45 which is wrapped around and slides on shaft 35. Spring 45 has its travel limited on shaft 35 by a knub or clamp and/or retaining device on shaft 35 near gripper 37 end of shaft which spring 45 butts up against preventing it from slipping off shaft 35. Spring 45 has its travel limited in the opposite direction by the slideable spring housing 46 that contains said spring. For example: When spring housing 46 is pushed in a direction away from handle 33, spring 45 is compressed and when said pushing force is released, compressed spring 45 causes spring housing 46 to snap back to its original position. Jaws 38 are contained or attached to spring housing 46 and move synchronized to housing 46. When spring housing 46 is pushed in a direction away from handle 33, jaws are moving away from gripping 37 thus enlarging aperture 39. When said pushing force is removed from spring housing 46, jaws 38 are snapped back towards gripper 37, thus causing a tensioned force to be applied to needle cap 73 if it were inserted in aperture 39 as shown in FIG. 20.

Jaws 38 can be made of any material that would allow a force to be exerted on needle cap 73. Jaws 38 can be made in any form that would allow a force to be exerted on inserted needle cap 73. Jaws 38 can be in the form of a loop instead of separated as shown in FIG. 19. Jaws 38 can be in the form of a belt like apparatus or using in cinching action or any other device or mechanism that would allow positive retention of needle cap 73 (not shown). In the preferred embodiment shown (FIG. 19), the jaws 38 comprise spring steel and are contained in spring housing 46. FIG. 19 shows gripper 37. Gripper 37 can be made of any material that would allow a force to be applied to inserted needle cap 73. Gripper 37 can be in the form of a sharp point as in preferred embodiment. Gripper 37 can consist or comprise singly or in combination of points, serrations, knubs, sticky substances, rubbery substances, sharp knife like devices, or any other device, apparatus, mechanism or material that would provide a gripping action on a needle cap 73.

FIG. 19 shows an illustration of recoiling device 43 comprising chain 42 and clip 44. Recoiling device 43 is attached to handle 33 by hole 47. Recoiling device 47 can be of the type currently in use as a device for holding keys such as the type worn by many custodians that is attached to the belt or clothing by a clip or pin, and contains a chain which can be retracted or extended for use. It can also comprise any device that would allow cap holding tool 32 to remain attached to the user and retracted or extended for use.

Figure 21:
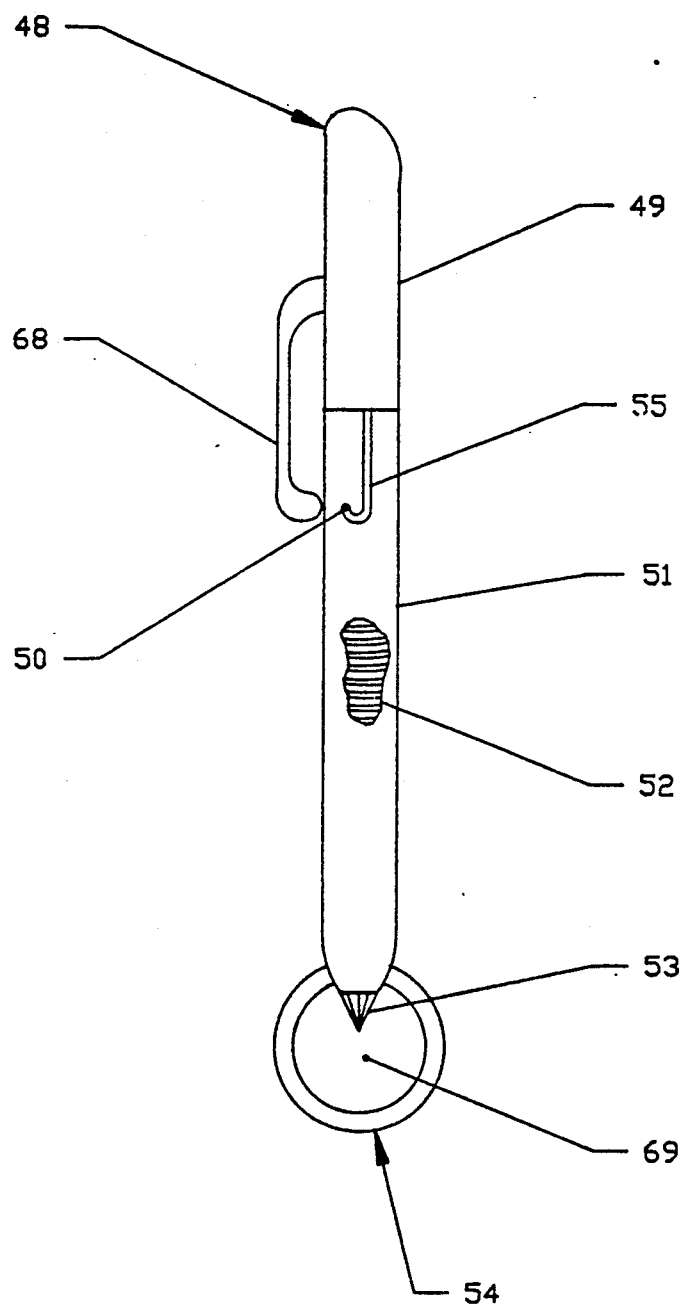
FIG. 21 shows a side view of pocket needle cap holding tool.

FIG. 21 shows pocket needle cap tool 48. Pocket needle cap tool 48 comprises handle 49, tubular container 51, internal transmission means 52, gripper 53, gripping loop 54, and clip 68. Pocket needle cap tool can be carried with the worker and kept in the pocket, much like a conventional writing pen is carried in a shirt pocket. In the preferred embodiment show, handle 49 is a continuation of tubular container 51 resembling the body of a ball point pen. Handle 49 can take any other form that would allow holding and operating needle cap tool 48 in a controlled manner. Handle 49 can be made of the same material as tubular container 51, or can comprise different materials as tubular container 51. Handle 49 can be attached to tubular container 51 in any manner that allows security of attachment, such as, screwed on, glued, laminated, molded, press fit, etc. In the preferred embodiment shown, handle 49 is screwed onto tubular body 51 in the same manner as a common ball point pen is screwed together. In the preferred embodiment of FIG. 21, gripping means control 50 is mostly contained inside tubular container 51, with the exception of a small knob that protrudes outside tubular container 51 through opening 55. The location and composition and form of gripping means control 50 may vary in different embodiments of the invention. In the preferred embodiment of FIG. 21, tubular container 51 contains and encloses internal transmission means 52. Any mechanism that would allow controlling a gripping force on inserted needle cap 73 in gripping loop 54 (FIG. 22) can be used. In the preferred embodiment of FIG. 21, internal transmission means 52 comprises and spring means which produces a tensioning force on gripping loop 54 causing said loop to constrict, or contract towards gripper 53 when internal transmission means 52 is in its relaxed, or non-compressed state. In other embodiments, transmission means 52 can comprise any mechanism, or device, that would allow a controlled grip and release on needle cap 73. Any of the components, methods, designs and materials of cap holding tool 32 (shown in FIG. 19) can be freely intermixed with pocket needle cap tool 48 (FIG. 21) singly or in combination. Conversely, any of the components, methods, designs and materials used in pocket needle cap tool 48 (FIG. 21) can be intermixed with pocket cap holding tool 32 (FIG. 19) singly or in combination. For example jaws 38 (FIG. 19) can be used on pocket needle cap tool 48 (FIG. 13) instead of gripping loop 54 and visa versa. In FIG. 21, clip 68 is attached to handle 49. In the preferred embodiment shown, clip 68 is designed to allow pocket needle cap tool 48 to be clipped to a shirt pocket in the same manner as a common ball point pen in clipped to a pocket. Any material and design suitable to accomplish this can be used.

From the description above, a number of advantages of my method and devices for the safe handling of hypodermic syringes become evident:

(a) All devices can be used on existing inventories of hypodermic syringes and needle caps, because the devices can be installed in the field by the user, or others, in an easy manner. This would result in a great savings since existing inventories of syringes and needle caps would not become obsolete and have to be destroyed.

(b) Remote locations of the world could be supplied devices with directions, in a fast manner so immediate implementation could be accomplished.

(c) Manufacturers would not have to change existing tooling and machining used in making syringes and needle caps, since the devices could be installed as an accessory to the needle cap/syringe.

(c) The devices could be shipped unattached to the needle cap so the user would have a choice of not using a device by not installing it on the needle cap if so desired or the manufacture can install them before shipment.

(e) The devices would be very inexpensive to manufacture so they could be made disposable which would fit in with current procedures.

(f) The devices lock the needle cap on the syringe after use, so the needle cap can't be knocked off later exposing workers, waste handlers and others to contaminated needle sticks.

(g) The use of these devices would greatly lower the risk of a major work site accident of health workers e.g.

accidental needle sticks, and may qualify for lower insurance premiums to those who employ the devices.

(h) Large profits could be made by manufactures and sellers of the devices due to the simple, low cost construction and small size of the devices.

(i) Users would be under less stress over long periods of time since they would not have to worry about an accidental needle stick.

(j) Future epidemics caused by secondary infections emanating from accidental needle stick victims may be eliminated or minimized.

OPERATION—FIGS. 1-22

FIG. 1 shows the conventional hypodermic syringe 71 and needle cap 73 in use today. The various devices and tools of the invention install on said syringe 71 and needle cap 73 without any structural changes being necessary. This allows existing inventories and manufacturing methods of syringe 71 and needle cap 73 to be utilized with little or no change required. The user can install said devices in the field, or the manufacturer can install them. The devices can be packaged, not installed, with the syringe.

Figure 7:
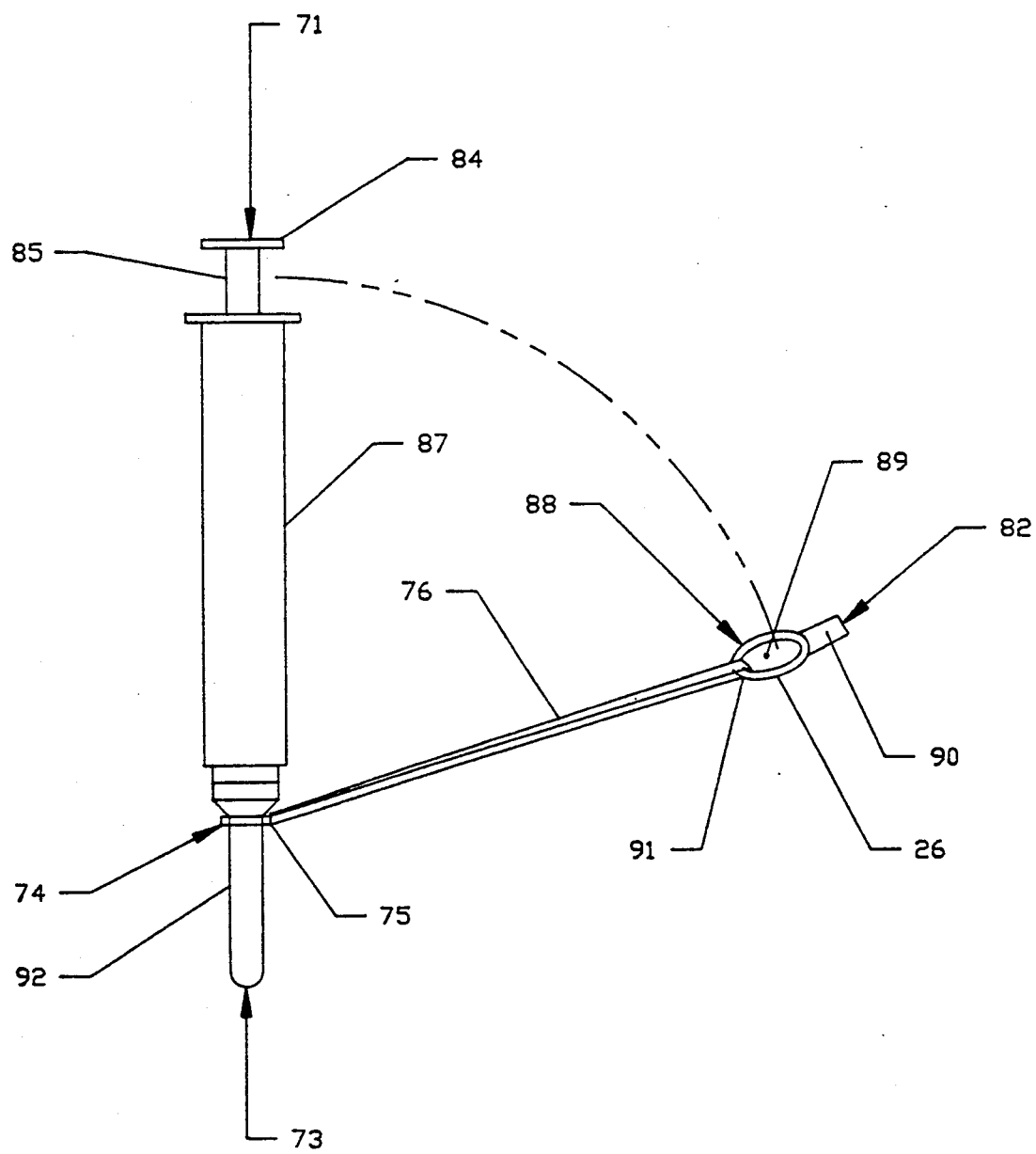
FIG. 7 shows a side view of the preferred embodiment of the invention with needle cap holding device installed and handle extended.

FIG. 5 shows the standard syringe 71, as needle cap holding device 82 is being installed on needle cap 73. Needle cap 73 is inserted through holding device aperture 80 of cap gripping end 74. Cap gripping end 74 is then slide up around needle cap barrel rim 92 till it is held snugly in place by gripping apparatus 81 or in alternate embodiments, smooth gripping apparatus 83 (shown in FIGS. 3 and 4). FIG. 5 shows needle cap flange 63 which may if desired, be used as an abutment restriction the furthermost travel of cap gripping end 74 needle cap barrel rim 92. FIG. 8 shows as side view of needle cap 14 as it appears attached to needle cap 73 after being installed as described above. The installation procedure described above can be carried out with the needle cap 73 on the syringe or detached from the syringe. With needle cap holding device 82 installed as shown in FIG. 8, handle 76 is extended providing a long gripping appendage for the user to hold on to. The length of said handle 76 allows the user to hold the needle cap 73 away from the hand and fingers, so the hypodermic needle 72 and attached syringe can be inserted into needle cap opening 79 of said needle cap 73, in a safe controlled manner. After needle 72 is safely inserted in needle cap 73, (as shown in FIG. 7), the user can move handle 76 up to attach out of the way on syringe 71 as shown in FIG. 6. The attachment of handle 76 to syringe 71 by plunger clamping device 88 (FIG. 6) serves and additional purpose of locking needle cap 73 to syringe 71 so it cannot be knocked off accidentally.

In the preferred embodiment shown in FIG. 6, needle cap holding device 82 is installed on needle cap 73 as stated above, and secured to syringe 71 around plunger neck 85 by loop 26 of plunger clamping device 88. This would be the normal stored or resting state of syringe 71 before or after use. In said state, the needle cap 73 is securely held in place, because any downward movement of said needle cap 73 from syringe body 87 would be stopped by the travel restriction imposed by the attachment of needle cap holding device 82 to plunger neck 85 at one end, and needle cap 73 at the other end as shown. To operate the syringe starting from the above stored state, the user grasps tab 90 pulling it up and over plunger button 84. The elastic material of loop 26 allows sufficient stretching and enlarging of plunger end aperture 89 to permit plunger clamping device 88 to easily clear plunger neck 85 and plunger button 84. This frees plunger clamping device 88 from attachment to said plunger neck 85 and allows handle 76 to be extended as shown in FIG. 7. Handle attachment 75 provides the flexibility as previously described, to allow extension of said handle 76 and support of needle cap 73. In this position, handle 76 supplies the user a hand or finger hold sufficient distance from needle cap 73 to allow safe withdrawal (or reinsertion) of syringe 71 from needle cap 73 as shown in FIG. 8. This is accomplished by the user holding handle 76 with one hand, and plunger syringe 71 away from needle cap 73 with the other hand. Some syringe and needle cap designs require a twisting action to unlock the needle cap. This can easily be provided by simply twisting the syringe 71 on withdrawal. After withdrawal, the user can continue holding needle cap holding device 82 by the handle 76 or with a finger in aperture 89 or any other manner that is comfortable including setting needle cap holding device 88 down or placing it in the pocket. The user then uses the syringe in the normal manner.

To recap the syringe after use, (FIG. 8) the user holds handle 76 with one hand, as described above, and with the other hand, reinserts syringe 71 and its attached needle 72 into needle cap opening 79 of needle cap 73. With the syringe 71 reinserted in needle cap 73 as shown in FIG. 7, the user attaches plunger clamping device 88 to syringe 71 by pulling tab 90 up to plunger button 84 and stretching loop 26 over plunger button 84 so loop 26 becomes positioned around plunger neck 85 as shown in FIG. 6. This safely recaps syringe 71 and allows it to be disposed of, keeping the users' hands and fingers a safe distance from the contaminated needle at all times. As shown in FIG. 6, needle cap 73 is safely secured so it can't be knocked off later, exposing waste handlers and others to a contaminated needle stick.

Figure 9:
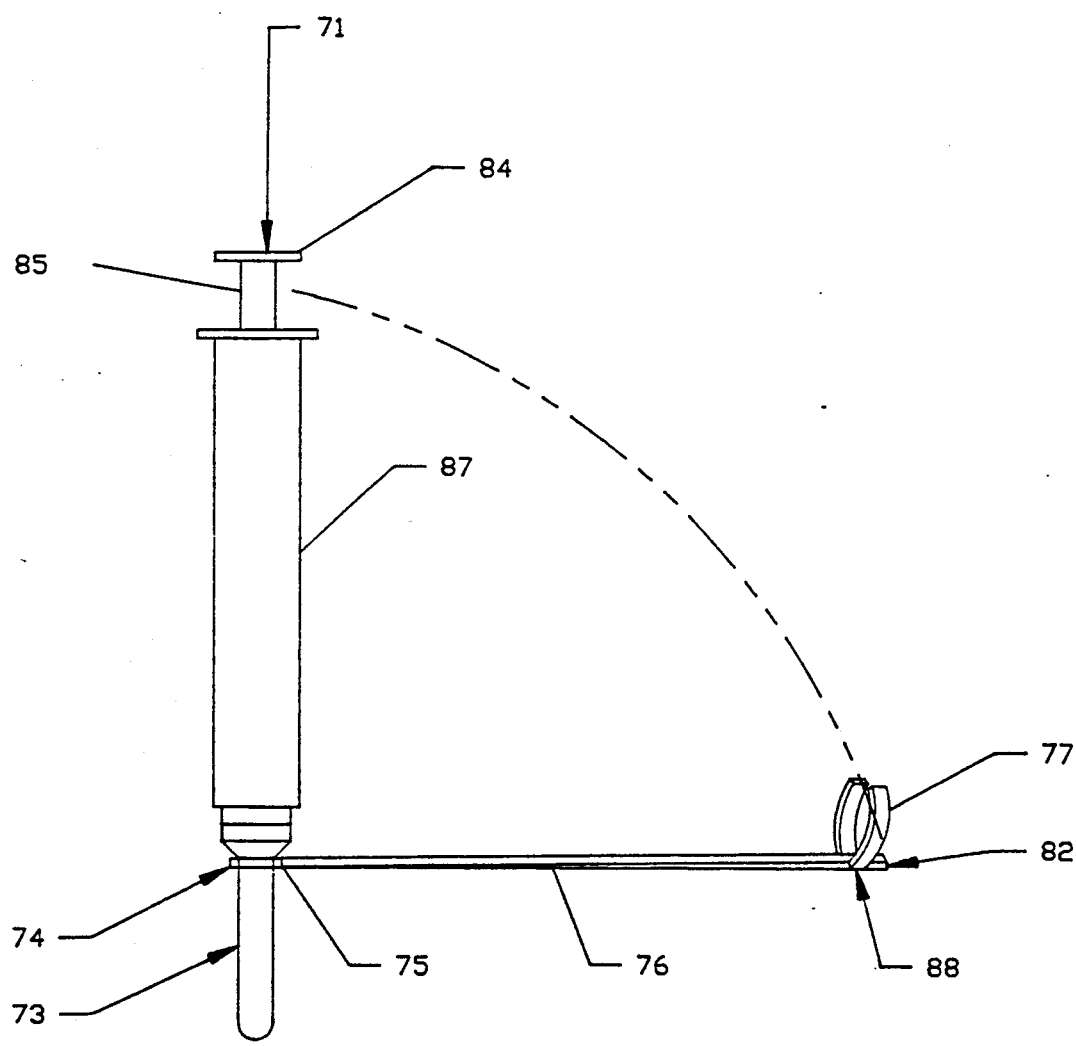
FIG. 9 shows a side view of an alternate embodiment side view of the needle cap holding device attached to need cap and in the extended position with a pair of clamps as the clamping device.
Figure 10:
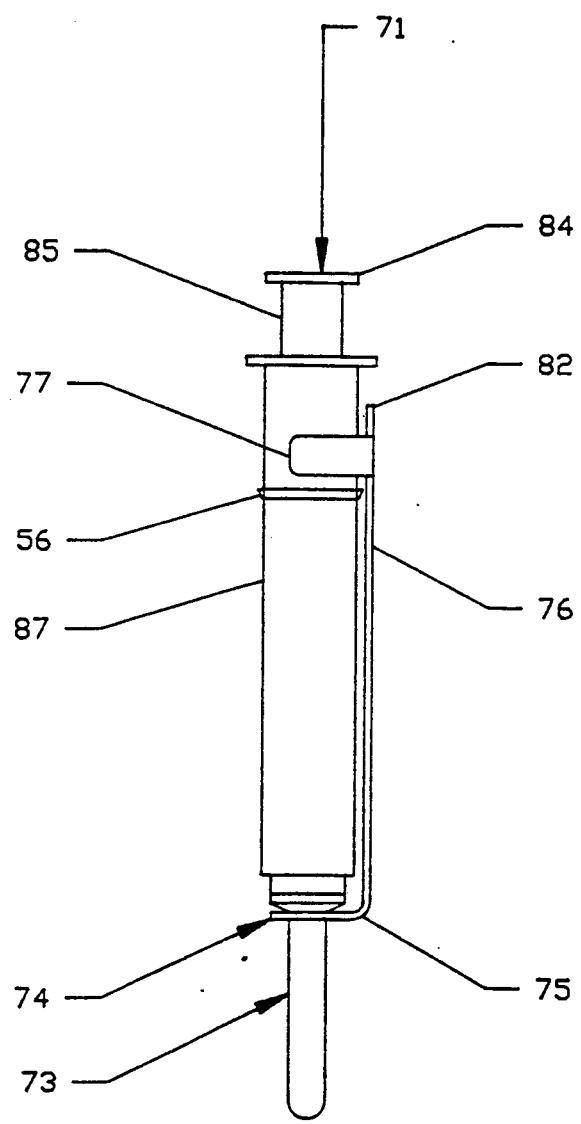
FIG. 10 shows a side view of the embodiment of FIG. 9 with handle attached to syringe body.

FIG. 9 shows and alternate embodiment of needle cap holding device 82. Instead of loop 26 as in the preferred embodiment of (FIG. 2), clamps 77 is used comprising a pair of clamps (FIG. (. Due to their open ended design, clamps 77 allows the user to clamp around plunger neck 85 from the side without having to be pulled over plunger button 84. Clamps 77 can be attached around syringe body 87 (FIG. 10) instead of around plunger neck 85 if said clamps 77 are molded or attached to handle 76 a suitable distance to allow this embodiment. Said embodiment would have the disadvantage that clamps 77 could be slipped down body 87 which would not securely lock needle cap 73 on to syringe 77. This problem can be corrected by attaching some sort of retaining device on the body of the syringe that would eliminate the clamps 77 downward travel on the syringe body 87. For example, a ring 56 (FIG. 10) can be inserted around or attached to syringe body 87 that would serve as a abutment to downward travel on syringe body 87 by clamps 77 which would keep needle cap 73 secured in place.

FIG. 3 shows an alternate embodiment with clamping device spring 25 replacing loop 26 of the preferred embodiment (FIG. 2). The embodiment of FIG. 3 operates the same as the preferred embodiment (FIG. 2) with the spring being stretched to go over plunger button 84 and constricting around plunger neck 85 holding needle cap 73 securely in place and handle 76 out of the way similar to FIG. 6.

FIG. 4 shows still another embodiment with ridged loop 27 replacing loop 26 of the preferred embodiment of FIG. 2. This embodiment (FIG. 4) has a plunger end aperture 89 large enough to fit over plunger button 84 without having to be stretched. This embodiment has a spring attachment 28 for handle attachment 75. This allows the ridged loop 27 to be placed over plunger button 84 and around plunger neck 85 with the spring attachment 28 creating a tension holding the plunger clamping device 88 in place around plunger neck 85 and creating a tensioning force on needle cap 73 securing it to the syringe. The spring attachment 28 serves to act as a hinge and support for cap gripping end 74 when ridged loop 27 is removed from around plunger neck 85 and over button 84 as handle 76 is extended for use in a similar manner to that described for the preferred embodiment of FIG. 2 except no stretching of plunger end aperture 89 is required. This embodiment (FIG. 4), can also comprise an alternate spring attachment 70 for ring attachment 91. This embodiment can also have both spring attachment 28 and alternate spring attachment 70. This embodiment can comprise a continuous spring forming handle 76 and attaching cap gripping end 74 to plunger clamping device 88 (not shown). Or in yet another embodiment of FIG. 4, a single spring could be placed anywhere in handle 76 (not shown). Other devices or materials other than springs can be used in the above embodiments.

FIG. 12 shows another embodiment of the invention. Syringe ring clamp 58 slides up on syringe body 87 so handle indent 57 can be inserted in handle insert 59 for the resting or stored position of needle cap holding device 82. Syringe ring clamp 58 can be retained by clamp or other device or process if desired.

FIG. 14 shows another embodiment of the invention. Syringe 71 is inserted into body clamp 61 and said body clamp 61 is slide up on syringe body 87 so female receptacle 60 can be inserted on male protrusion 62 for the resting or stored position of needle cap holding device 82. Body clamp 61 can be retained as described above if desired.

FIG. 18 shows circular metallic washer 29 of cap gripping end 74 as needle cap 73 is being inserted into concave holding device aperture 80 from concave side 31. In this embodiment, the gripping apparatus 81 comprises stamped teeth 30 which form a concave aperture 80. The design of the teeth allow the needle cap 73 to be inserted from concave side 31, but will not allow pulling out in the opposite direction. Washer 29 can be inserted till it meets the abutment of needle cap flange 63 if so desired. Numerous variations of this device are possible as previously described.

FIG. 15 shows an alternate embodiment of needle cap holding device 82 comprising a hook 64 with opening 65. Hook 64 is grasped by tab 90 and pulled up to neck 85 and opening 65 allows connection of hook 64 around neck 85. Conversely, to ready the syringe for use, simply unhook hook 64 from around neck 85 and extend handle 76. The flexible material or device used for ring attachment 91 or alternately, handle attachment 75 will allow easy manipulation of hook 64 during the above operations. Also, an elastic or spring device can be incorporated within needle cap holding device 82 to provide a tensioning force if desired. Hook 64 can be made to attach to finger grips 86 instead of around plunger neck 85 (not shown). Hook 64 can be made to attach around plunger neck 85 and over finger grips 86 (not shown). Hook 64 can comprise a plurality of hooks or clamps that would attach to finger grips 86 (not shown).

FIG. 16 shows an alternate embodiment of needle cap holding device 82 that comprises a cap 66 and cavity 67 in a plunger clamping device 88. The embodiment attaches to the needle cap as stated above. To operate, the user grasps tab 90 and pulls plunger clamping device 88 up to plunger button 84 where cavity 67 is placed over plunger button 84 in a capping motion. This secures handle 76 in the retracted position and locks needle cap 73 in place so it can't be knocked off. To extend the handle, the user simply removes cap 66 by grasping tab 90, and with an uncapping motion removes the cap 66 from plunger button 84, extending handle 76 for use. The flexible material or device comprising ring attachment 91 allows easy manipulation during this process. Also, an elastic or spring device or material can be incorporated into needle cap holding device 82 to provide a tension force.

FIG. 19 shows cap holding tool 32. Cap holding tool 32 can be attached to the user, so it won't be lost and will be available for immediate use. Clip 44 allows recoiling device 43 to attached to the users belt, pocket, clothing etc. The extendable chain 42 is attached to hole 47 of cap holding tool 32. This keeps cap holding tool 32 connected to the user and allows him to withdraw and retract cap holding tool 32 as required for use. This operation would be similar to the way many janitors withdraw and retract keys attached to a recoiling device for opening doors etc. The cap holding 32 can be used without recoiling device 43 being incorporated if desired.

To operate needle cap tool 32 (FIG. 19), the user holds handle 33 and expands aperture 39 by pushing on gripping means control 34 using the finger or thumb of the same hand. With the other hand, the user then inserts syringe 71 and its attached needle cap 73 into aperture 39 and releases gripping means control 34 causing a gripping action which retains inserted needle cap 73 in cap holding tool 32. The user then withdraws syringe 71, from the retained needle cap 73, exposing needle 72 for use. The cap holding tool 32 and the retained needle cap 73 (FIG. 20), can be released to be retracted by recoiling device 43. This places cap holding tool 32 and retained needle cap 73 out of the way on the users' body, thus freeing both hands of the user to operate syringe. After syringe 71 is used, (FIG. 20) the user can grasp handle 33 with one hand, and extend cap holding tool 32 and contained needle cap 73 away from the user's body for reinsertion of the syringe 71/needle 72 into the needle cap opening 79 of retained needle cap 73. Once the reinsertion process is complete, the user releases retained needle cap 73 and attached syringe 71 from gripping means 41 by manipulating or pushing on gripping means control 34, and withdrawing the reattached needle cap 73 syringe 71 combination with a withdrawing motion of the other opposite hand, thus safely recapping syringe needle 72. The syringe 71 needle cap 73 combination can now be safely disposed off, and cap holding tool 32 can be allowed to recoil up out of way on the users body ready for future use.

Figure 22:
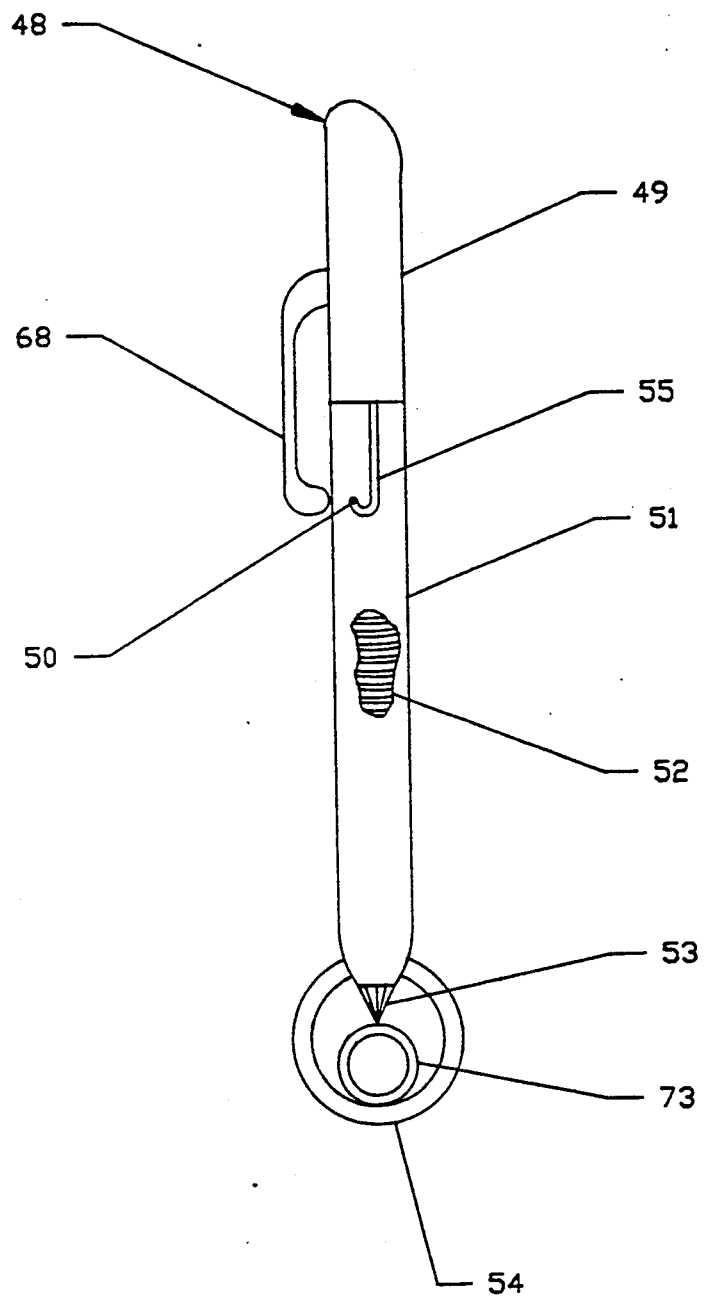
FIG. 22 shows a side view of the embodiment of FIG. 21 with needle cap retained therein.

FIG. 21 shows the preferred embodiment of pocket needle cap tool 48. Pocket needle cap tool 48 is designed to be carried around with the worker available for immediate use, much like the standard ball point pen is carried in a users pocket. The size, shape and clip 69 allow this. To operate pocket needle cap tool 48, the user holds said tool in one hand by handle 49 and pushes gripping means control 50 with the finger of one hand, thereby expanding gripping loop 54 enabling needle cap 73 of attached syringe 71 to be inserted into loop aperture 69. The user then releases internal transmission means 52 by manipulation of gripping means control 50 which creates a constricting or gripping force on inserted needle cap 73. The user then withdraws syringe 71 from pocket needle cap holding tool 48 exposing needle 72 leaving needle cap 73 retained in pocket needle cap holding tool 48 as shown in FIG. 22. The user can put pocket needle cap holding tool 48 and retained needle cap 73 down, or back in his pocket freeing both hands for syringe 71 use.

After syringe 71 has been used, the user grasps handle 49 of pocket needle cap holding tool 48 with one hand, and reinserts needle 72 of attached syringe 71 into needle cap opening 79 of retained needle cap 73 thus locking the cap on. The user then releases needle cap 73 by manipulating gripping means control 50, and withdraws needle cap 73 and attached syringe 71 from pocket needle cap tool 48 with the opposite hand, thus safely recapping syringe needle 72 for disposal.

SUMMARY, RAMIFICATIONS, AND SCOPE

Thus the reader will see that the method and devices of the invention provide a highly reliable, lightweight, yet economical device which will allow the user to easily, and safely handle contaminated syringe needles in a controlled manner, keeping the exposed bare hands and fingers a safe distance from said needle at all times. In addition, the device locks the needle cap positively on so it can't be knocked loose after exposing waste handles and others to contaminated needle sticks. Furthermore, the invention has the additional advantages in that The devices do not require any modification of existing syringes and needle caps, and therefore can be supplied as an inexpensive, disposable, accessory for existing syringes and needle caps.

The devices can be easily installed by the user in the field, or by the manufacturer if so required.

The devices operate very simply and can be supplied with simple picture directions minimizing the need for language translation.

The devices are very durable and inexpensive to manufacture.

The devices are always available for use when attached to the syringe or to the user so loss or unavailability would not be a factor.

The devices allow the user to safely use hypodermic syringes with bare hands so procedures would not have to be changed.

The devices would prevent or drastically reduce a major worksite accident of syringe users, needle sticks.

Future generations would benefit from a lesser rate of epidemics caused by secondary infections of needle stick victims.

Although the description above contains many specificities, these should not be construed as limiting the scope of the invention but as merely providing illustrations of some of the presently preferred embodiments of this invention. Any of the components, materials, forms of the devices may be freely intermixed causing new embodiments, for example; gripping apparatus 81 can be used in any of the embodiments shown in the drawings, specification, or other embodiments. Alternately, smooth gripping apparatus 83 can be used in any embodiment shown or otherwise developed. Gripping apparatus 81 can be contained as side open embodiment as in jaws 38. Cap gripping end 74 can be used on any embodiment including the ones shown in the drawings and specification. Handle 76 can be attached in such way that it expands away from the syringe 71 in a jack knife manner (not shown) instead of in a pull away manner from the syringe 71 as shown in FIGS. 7 and 9. That is to say, the syringe would be positioned like the handle of a jack knife, and the handle 76 would be pulled away from the syringe for extension in a similar manner as a blade is pulled from a pocket knife (not shown). A clamping mechanism can be installed near the pivoting point in this embodiment or in the usual places on the handle 76. Handle 76 can be constructed comprising no clamping mechanism is desired, instead using the mechanism in a needle cap. This would allow the handle to fold along the syringe body 87 without being attached to it (not shown). Needle cap 73 can be redesigned to include or comprise any of the components of this invention singly or in combination. Cap gripping end 74 can also comprise a redesigned needle cap that has said end 74 formed from or molded from or attached in any manner to said needle cap. Handle 76 can include a redesigned needle cap that has said handle 76 formed from or molded from or attached to said needle cap in any manner. Syringe 71 can be redesigned to include various molded or formed parts incorporated one said syringe 71 such as ring 56, or handle insert 59 or protrusion 62 or any other attaching device attached or formed or molded on syringe 1. All devices can be intermixed in position of needle cap 73 syringe 71 etc. The sizes of all devices and their components can vary to match or be functional with the various types of existing syringes and hypodermic needle caps.

Thus the scope of the invention should be determined by the appended claims and their legal equivalents, rather than by examples given.

I claim:

1. A needle cap holding device for uncapping and recapping a needle cap over a hypodermic needle on a hypodermic syringe comprising:
   (a) a handle including a hand holding end and a cap gripping end that includes means for attaching said handle to said needle cap, and
   (b) attachment means for attaching said handle to said cap gripping end, in order to allow said handle to be moved repeatedly toward or away from said syringe while said gripping end is attached to said needle cap and said needle cap is attached on said syringe, and
   (c) a clamping means attached to said handle for securing the hand holding end of said handle on said syringe while the gripping end is attached to said needle cap and said needle cap is attached on said syringe, and
   (d) a means for locking said needle cap onto said syringe, whereby a user can extend said handle a suitable distance from the capped needle and remove said needle cap including the attached said holding device from said syringe and said needle, leaving said syringe and said needle unaltered for use, and replace said needle cap on said needle keeping the hands and fingers a safe distance from said needle, and secure said handle on said syringe for storage and positive retention of said needle cap on said syringe.

2. The needle cap holding device of claim 1 wherein said clamping means comprises a spring.

3. The needle cap holding device of claim 1 wherein said clamping means comprises a loop that attaches on the button neck of said syringe.

4. The needle cap holding device of claim 1 wherein said clamping means comprises an elastic loop that attaches on the neck of said syringe.

5. The needle cap holding device of claim 1 wherein said clamping means comprises a cap that attaches on the button of said syringe.

6. The needle cap holding device of claim 1 wherein said clamping means comprises a hook that attaches on the plunger neck of said syringe.

7. The needle cap holding device of claim 1 wherein said clamping means comprises a ring that attaches on the plunger neck of said syringe.

8. The needle cap holding device of claim 1 wherein said handle comprises a spring.

9. The needle cap holding device of claim 5 wherein said cap comprises grasping means for holding said handle and removing and replacing said clamping means.

10. A method of safely uncapping and recapping a hypodermic needle cap on a hypodermic needle on a hypodermic syringe comprising:
    (a) holding the handle of a needle cap holding device with the needle cap attached to said device, the needle cap holding device comprising a handle including a hand holding end and a cap gripping end that includes means for attaching said handle to said needle cap, attachment means for attaching said handle to said cap gripping end, clamping means attached on said handle for securing the hand holding end of said handle on said syringe, and a means for locking said needle cap onto said syringe, and
    (b) holding the syringe with the opposite hand and withdrawing said syringe and attached said needle from said needle cap, and
    (c) reinserting said needle in said needle cap by holding said handle with one hand and said syringe with the opposite hand, and
    (d) securing said handle on said syringe, removably locking the needle cap in place for storage or disposal.

* * * * *